(12) United States Patent
Liping et al.

(10) Patent No.: US 9,614,162 B2
(45) Date of Patent: Apr. 4, 2017

(54) LIGHT-EMITTING DEVICES COMPRISING EMISSIVE LAYER

(71) Applicant: NITTO DENKO CORPORATION, Osaka (JP)

(72) Inventors: Ma Liping, San Diego, CA (US); Shijun Zheng, San Diego, CA (US); David T. Sisk, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 632 days.

(21) Appl. No.: 14/108,605

(22) Filed: Dec. 17, 2013

(65) Prior Publication Data

US 2014/0167014 A1 Jun. 19, 2014

Related U.S. Application Data

(60) Provisional application No. 61/738,315, filed on Dec. 17, 2012.

(51) Int. Cl.
| | |
|---|---|
| *H01L 51/00* | (2006.01) |
| *H01L 51/50* | (2006.01) |
| *C09K 11/06* | (2006.01) |
| *H05B 33/14* | (2006.01) |
| *C07D 401/14* | (2006.01) |
| *C07D 413/14* | (2006.01) |
| *C07D 401/04* | (2006.01) |

(Continued)

(52) U.S. Cl.
CPC ........ *H01L 51/0071* (2013.01); *C07D 235/18* (2013.01); *C07D 401/04* (2013.01); *C07D 401/14* (2013.01); *C07D 403/10* (2013.01); *C07D 413/14* (2013.01); *C09K 11/06* (2013.01); *H01L 51/0052* (2013.01); *H01L 51/504* (2013.01); *H01L 51/5012* (2013.01); *H01L 51/5016* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *H01L 51/006* (2013.01); *H01L 51/0059* (2013.01)

(58) Field of Classification Search
CPC .................................................. H01L 51/0071
USPC ....................................................... 428/690
See application file for complete search history.

(56) References Cited

U.S. PATENT DOCUMENTS

| | | |
|---|---|---|
| 6,620,529 B1 | 9/2003 | Ise et al. |
| 6,835,469 B2 | 12/2004 | Kwong et al. |
| 6,984,934 B2 | 1/2006 | Moller et al. |

(Continued)

FOREIGN PATENT DOCUMENTS

| | | |
|---|---|---|
| CN | 101400658 | 4/2009 |
| GB | 2408209 | 5/2005 |

(Continued)

OTHER PUBLICATIONS

Yu et al, A yellow-emitting iridium complex . . . high color quality and efficiency, Journal of Organometallic Chemistry 693 (2008) 1518-1527.*

(Continued)

*Primary Examiner* — Doris Lee
(74) *Attorney, Agent, or Firm* — K&L Gates LLP; Brent A. Johnson; Louis C. Cullman

(57) ABSTRACT

Light-emitting devices comprising an fluorescent emissive layer, and three different phosphorescent emissive layers are described herein.

52 Claims, 5 Drawing Sheets

(51) Int. Cl.
   *C07D 235/18* (2006.01)
   *C07D 403/10* (2006.01)

(56) References Cited

U.S. PATENT DOCUMENTS

| | | | |
|---|---|---|---|
| 7,053,547 | B2 | 5/2006 | Lu et al. |
| 7,109,652 | B2 | 9/2006 | Tsai et al. |
| 7,321,193 | B2 | 1/2008 | Antoniadis et al. |
| 7,332,860 | B2 | 2/2008 | Hatwar et al. |
| 7,652,280 | B2 | 1/2010 | Li et al. |
| 7,678,959 | B2 | 3/2010 | Okada et al. |
| 7,834,546 | B2 | 11/2010 | Krummacher et al. |
| 8,426,040 | B2 | 4/2013 | Zheng et al. |
| 2002/0191130 | A1 | 12/2002 | Liang et al. |
| 2005/0106710 | A1 | 5/2005 | Friedman et al. |
| 2007/0103056 | A1 | 5/2007 | Cok et al. |
| 2007/0222367 | A1* | 9/2007 | Hosoda ............ H01L 27/3213 313/503 |
| 2008/0014464 | A1 | 1/2008 | Kawamura |
| 2008/0116784 | A1 | 5/2008 | Krummacher et al. |
| 2008/0311178 | A1 | 12/2008 | Ishikura et al. |
| 2009/0115319 | A1 | 5/2009 | Kim et al. |
| 2009/0134783 | A1 | 5/2009 | Lin et al. |
| 2009/0184633 | A1 | 7/2009 | Kadoma et al. |
| 2010/0060154 | A1 | 3/2010 | Nomura et al. |
| 2010/0326526 | A1 | 12/2010 | Zheng et al. |
| 2011/0140093 | A1* | 6/2011 | Zheng ................. C07D 235/18 257/40 |
| 2011/0251401 | A1 | 10/2011 | Zheng et al. |
| 2012/0104277 | A1 | 5/2012 | Morren |
| 2012/0179089 | A1 | 7/2012 | Sisk et al. |
| 2012/0197179 | A1 | 8/2012 | Khan et al. |
| 2012/0223633 | A1 | 9/2012 | Yoshinaga et al. |
| 2012/0223635 | A1 | 9/2012 | Mochizuki et al. |
| 2013/0140534 | A1 | 6/2013 | Lai et al. |
| 2014/0163237 | A1 | 6/2014 | Sisk |

FOREIGN PATENT DOCUMENTS

| | | |
|---|---|---|
| JP | 02072370 | 3/1990 |
| JP | 2002275179 | 9/2002 |
| JP | 2006156445 | 6/2006 |
| JP | 2007-095444 | 4/2007 |
| KR | 2010075079 | 7/2010 |
| WO | WO0014174 | 3/2000 |
| WO | 2004020388 | 3/2004 |
| WO | WO2004/049465 | 6/2004 |
| WO | 2006101735 | 9/2006 |
| WO | 2006130302 | 12/2006 |
| WO | 2008/052350 | 5/2008 |
| WO | WO 2009/009695 | 1/2009 |
| WO | 2009103165 | 8/2009 |
| WO | 2010044607 | 4/2010 |
| WO | 2011008560 | 1/2011 |
| WO | 2011109671 | 9/2011 |
| WO | 2012009283 | 1/2012 |
| WO | WO2012037269 | 3/2012 |
| WO | WO2012064987 | 5/2012 |
| WO | WO2012088294 | 6/2012 |
| WO | 2012103380 | 8/2012 |
| WO | 2014099864 | 6/2014 |

OTHER PUBLICATIONS

Aratani, Sukekazu et al., "Collimated Light Source using Patterned Organic Light-Emitting Diodes and Microlens", Japanese Journal of Applied Physics, vol. 49, No. 4, pp. 42101-1 (2010).
Schwartz, Gregor et al., "Harvesting Triplet Excitons from Fluorescent Blue Emitters in White Organic Light-Emitting Diodes", Advanced Materials, vol. 19, No. 21, pp. 3672-3676 (2007).
International Search Report for PCT/US2013/075584 mailed on Dec. 17, 2013.
G. Gustafsson, et al., "Flexible light-emitting diodes made from soluble conducting polymers," Nature, vol. 357, No. 6378, pp. 477-479, 1992.
U.S. Appl. No. 14/102,138, filed Dec. 10, 2013, Zheng, Shijun, Nitto Denko Corporation.
Yiru Su and Stephen R. Forrest, Enhanced light out-coupling of organic light-emitting devices using embedded low-index grids; *Nature Photonics*, 2008,2, 483-487.
Sun, Gang et al., TD-DFT and LDM studies of the electronic spectrum properties of 2-(2'-pyridyl)benzimidazole derivatives and their related complexes , Journal of Molecular Structure: THEOCHEM (2010), 955(1-3), 7-13.
Jan Birnstock, Tobias W. Canzler, Michael Holfmann, Giang Huang, and Tilmann Romainczyk, Highly efficient white Top-emission PIN OLEDs for display and lighting application; 2010 SID, 774, SID 10 Digest.
Hiroshi Kanno, Yiru Sun, and Stephen R. Forrest, High-efficiency top-emission white-light-emitting organic electrophosphorescent devices; Appl. Phys. Lett. 86, 263502(2005).
Chi-Che Liu, Su-Hao Liu, Kun-Cheng Tien, Min-Hung Hsu, Hong_Wer Chang, Chih-Kai Chang, Chih-Jen Yang, and Chung-Chih Wu, Microcavity top-emitting organic light-emitting devices integrated with diffusers for simultaneous enhancement of efficiencies and viewing characteristics; Appl. Phys. Lett. 94, 103302(2009).
H. Riel, S. Karg, T. Beierlein, and W. Rieß, Tuning the emission characteristics of top-emitting organic light-emitting devices by means of a dielectric capping layer: An experimental and therorotical study; J. Appl. Phys. 94, 5290(2003).
Peng et al., "5-Aminolevulinic Acid-Based Photodynamic Therapy. Clinical Research and Future Challenges", Cancer, Jun. 15, 1997, vol. 79, No. 12, pp. 2282-2308.
Chen et al., "Versatile, Benzimidazole/Amine-Based Ambipolar Compounds for Electroluminescent Applications: Single-Layer, Blue, Fluorescent OLEOs, Hosts for Single-Layer, Phosphorescent OLEOs", Advanced Functional Materials, 2009, vol. 19, pp. 2661-2670.
Gustafsson et al. "Flexible Light-Emitting Diodes Made from Soluble Conducting Polymer," Nature, Jun. 11, 1992, vol. 357, pp. 477-479.
Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-173.
Li et al., "Synthesis and Functional Properties of Strongly Luminescent Diphenylamine End-Capped Oligophenylenes", American Chemical Society, 2004, vol. 69, pp. 921-927.
International Search Report and Written Opinion in PCT Application No. PCT/US2012/022792, dated May 7, 2012.

* cited by examiner

| NM-1 (600nm) |
| Mg:Ag(20nm, 1:3) |
| NPB(100nm) |
| LIF(1nm) |
| TPBI(30nm) |
| Host-1:YE-01(30nm, 6 %) |
| Host-2: Ir(ppy)$_3$(3.5nm, 6 %) |
| Host-1:Ir(piq)2acac(1nm,10 %) |
| Host-1:BE-3 (15nm, 6 %) |
| NPB(30nm) |
| NPB:MoO3(10nm, 10 %) |
| MoO$_3$(5nm) |
| Al(100nm) |
| Glass Substrate |

LIGHT-EMITTING DEVICES COMPRISING EMISSIVE LAYER

CROSS REFERENCE TO RELATED APPLICATIONS

The present application claims the benefit of U.S. Provisional Application Ser. No. 61/738,315 filed Dec. 17, 2012, the entire contents of which are hereby incorporated by reference in their entirety.

FIELD

Some embodiments include top-emission white organic light-emitting diodes for lighting applications.

BACKGROUND

Organic light-emitting devices (OLED) are becoming increasingly important in lighting and display applications. However there are still significant improvements yet to be made for OLED technology that may help to encourage widespread use. For example, to replace a conventional light source with a OLED device, it may be helpful to raise power efficiency of OLED to a level that can compete with the level of conventional light sources. Generally, power efficiency is about 60-90 lm/W for fluorescent lamps. Therefore, it is desired to attain an efficiency of at least about 60 lm/W to help white OLED to compete as replacements for fluorescent lamps. The United States Department of Energy (DOE) described a 2015 target benchmark of about 150 lm/W (assuming CRI>80 and CCT=2700-3000K). Thus there is a need to further improve device efficiency.

SUMMARY

Incorporation of plural emissive layers into an OLED device may help to improve device efficiency while concurrently improving CRI values for the device. Some embodiments include an emissive construct comprising a fluorescent blue emissive layer, a phosphorescent red emissive layer contacting the fluorescent blue emissive layer; a phosphorescent green layer contacting the phosphorescent red emissive layer; and a phosphorescent yellow emissive layer contacting the phosphorescent green emissive layer. Some light emitting devices comprise the emissive construct described above disposed between an anode and a cathode.

Some embodiments include a white light emitting OLED device comprising in sequence from bottom to top, a substrate, an insulating layer coated on top of the substrate; a reflective and opaque anode disposed above the insulating layer; a hole injection layer disposed above the anode; a hole transport layer disposed above the hole injection layer; and the emissive construct described disposed above, an electron transporting layer disposed above the emissive construct; an electron injection layer disposed above the electron transporting layer; a semi transparent or transparent cathode disposed above the electron transport layer, a light emission enhancement layer disposed above the cathode; and a light scattering layer disposed above the light emission enhancement layer.

These and other embodiments are described in more detail herein.

DETAILED DESCRIPTION OF THE PREFERRED EMBODIMENT

The present application describes an emissive construct comprising a fluorescent emissive layer, and three phosphorescent emissive layers. For example, an emissive construct can comprise a fluorescent blue emissive layer; a phosphorescent red emissive layer contacting the fluorescent blue emissive layer; a phosphorescent green emissive layer contacting the phosphorescent red emissive layer, and which can be opposite to the fluorescent blue emissive layer (e.g. the phosphorescent green emissive layer and the fluorescent blue emissive layer can be on opposite sides of the phosphorescent red emissive layer); and a phosphorescent yellow emissive layer contacting the phosphorescent green emissive layer, and which can be opposite to the red emissive layer.

Figure 1A:
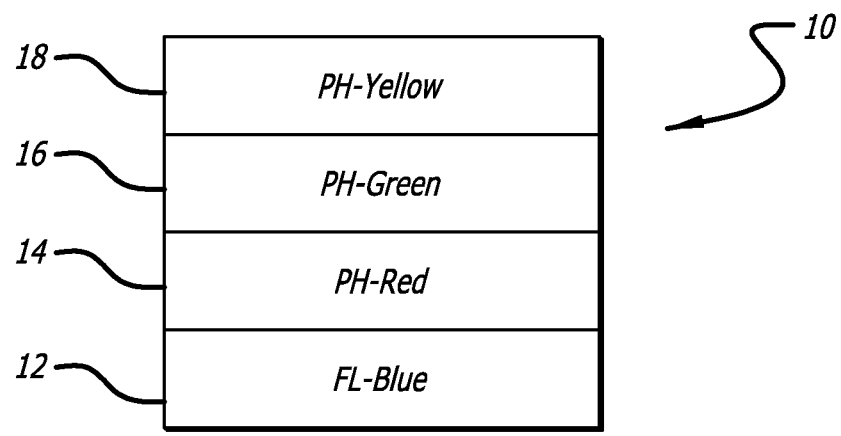
FIG. 1A is a schematic depiction of an embodiment of an emissive construct.

FIG. 1A is a schematic representation of the structure of some embodiments of a light emitting or emissive construct 10 described herein. The emissive construct 10 may include a fluorescent blue emissive layer 12. A phosphorescent red emissive layer 14 is disposed on fluorescent blue emissive layer 12. A phosphorescent green emissive layer 16 is disposed on phosphorescent red emissive layer 14. A phosphorescent yellow emissive layer 18 is disposed on phosphorescent green emissive layer 16.

Figure 1B:
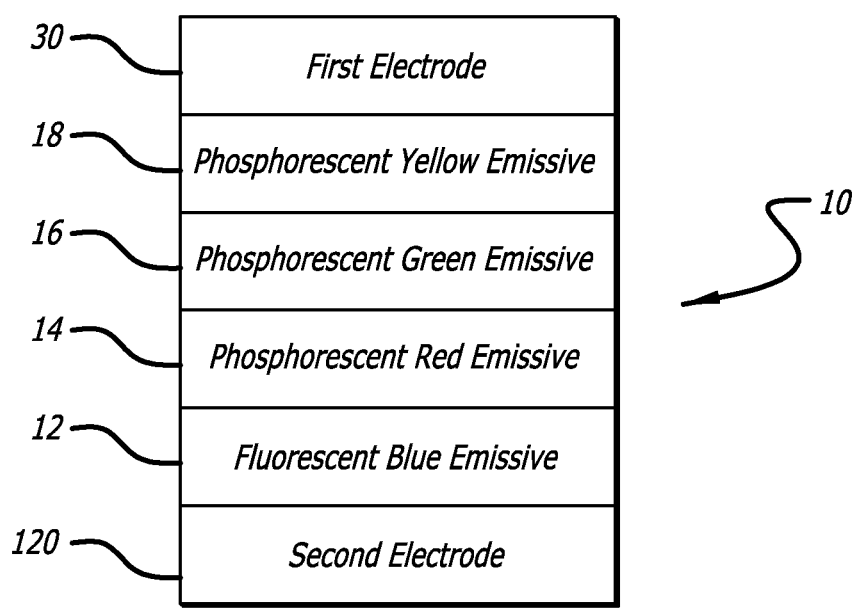
FIG. 1B is a schematic depiction of an embodiment of an emissive construct.

FIG. 1B is a schematic representation of the structure of some devices that include an emissive construct 10. In such a device, emissive construct 10 may be disposed between first electrode 30 and second electrode 120. The emissive construct 10 may include a fluorescent blue emissive layer 12. A phosphorescent red emissive layer 14 can be disposed on fluorescent blue emissive layer 12. A phosphorescent green emissive layer 16 can be disposed on phosphorescent red emissive layer 14. A phosphorescent yellow emissive layer 18 can be disposed on phosphorescent green emissive layer 16.

Figures 2, 3:
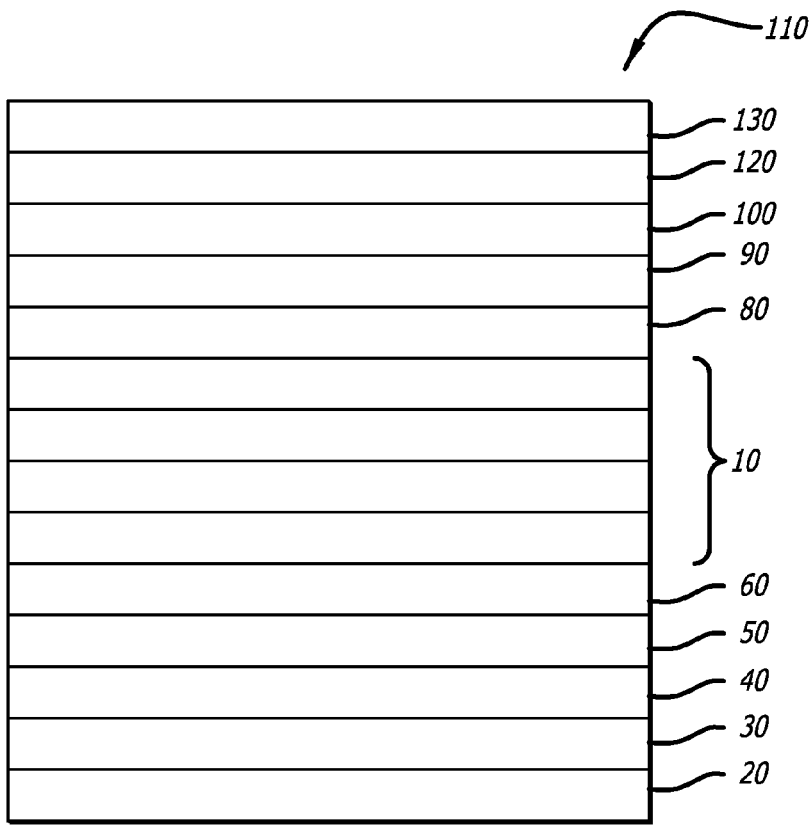
FIG. 2 is a schematic depiction of an embodiment of an organic light-emitting device.
FIG. 3 is a schematic depiction of an embodiment of an organic light-emitting device.

FIG. 2 is a schematic representation of the structure of some devices that include an emissive construct 10. In such a device, emissive construct 10 may be disposed between first electrode 30 and second electrode 120. In an embodiment, first electrode 30 may be a reflective anode disposed on substrate 20. Optionally, a hole injection layer 40 may be disposed on reflective anode 30. Optionally, a p-doped hole transport layer 50 may be disposed on hole injection layer 40. Optionally, a hole transport layer 60 may be disposed on p-doped hole transport layer 50. Optionally, the emissive construct 10 may be disposed on hole transport layer 60. Optionally, an electron transport layer 80 may be disposed on emissive construct 10 (phosphorescent yellow emissive layer 18). Optionally, an electron injection layer 90 may be disposed on electron transport layer 80. Optionally, a capping layer 100 may be disposed on electron injection layer 90. Optionally, the second electrode 120 may be disposed on capping layer 100. Optionally, a light scattering layer 130 may be disposed on second electrode 120. In one embodiment, the light scattering layer 130 may be plural nanostructures described in any of the following documents: U.S. Patent Publication No. 2012/0223635 (Ser. No. 13/410,812, filed Mar. 2, 2012, U.S. patent application Ser. No. 13/672,394, filed Nov. 8, 2012 and U.S. Provisional Application Ser. No. 61/696,085, filed Aug. 31, 2012, which are incorporated by reference for their description of appropriate nanostructured materials and outcoupling materials.

An emissive layer, e.g. a fluorescent blue emissive layer, a phosphorescent red emissive layer, a phosphorescent green emissive layer, or a phosphorescent yellow emissive layer, may comprise an emissive component and a host. The amount of the host in an emissive layer may vary. In some embodiments, the amount of a host in an emissive layer is in the range of from about 70% to nearly 100% by weight of the emissive layer, such as about 90% to about 99%, or about 97% by weight of the emissive layer. In some embodiments, the mass of the emissive component is about 0.1% to about 10%, about 1% to about 5%, or about 3% of the mass of the emissive layer. The emissive component may be a fluorescent and/or a phosphorescent compound.

A fluorescent blue emissive layer may emit blue light, such as light that has an emissive peak, or an average emission, of about 380 nm to about 500 nm, by fluorescence. In one embodiment, a fluorescent blue emissive layer, such as fluorescent blue emissive layer 12, comprises a host material and a dopant/emitter material. In some embodiments, the host may be a compound having a $T_1$ value (referring to the energy of the lowest lying triplet state) higher than the $T_1$ value of the dopant in the phosphorescent red emissive layer. In one embodiment, a host material may have a $T_1$ value greater than about 2.15 eV, about 2.20 eV, about 2.25 eV, about 2.3 eV, about 2.35 eV, and/or about 2.4 eV. Suitable hosts include, but are not limited to those described in co-pending applications United States Patent Publication No. 2011/0140093 (Ser. No. 13/033,473, filed Feb. 23, 2011); United States Patent Publication No. 2011/0251401 (Ser. No. 13/166,246, filed Jun. 11, 2011), U.S. Provisional Application No. 61/735,478, filed on 10 Dec. 2012), which are incorporated by reference herein for all disclosure related to chemical compounds. In some embodiments, the host compound may be any of the compounds below.

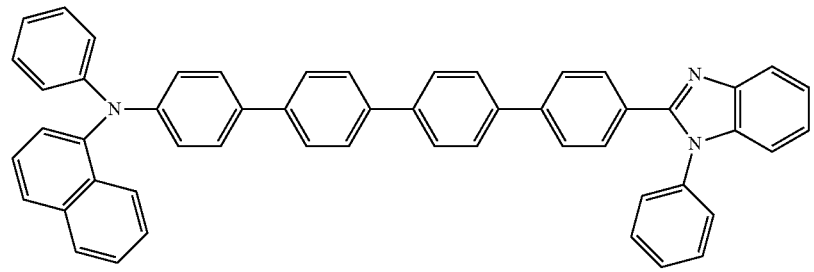

(Host-1)

9-(4'''-(1-phenyl-1H-benzo[d]imidazol-2-yl)-[1,1':4',1'':4'',1'''-quaterphenyl]-4-yl)-9H-carbazole

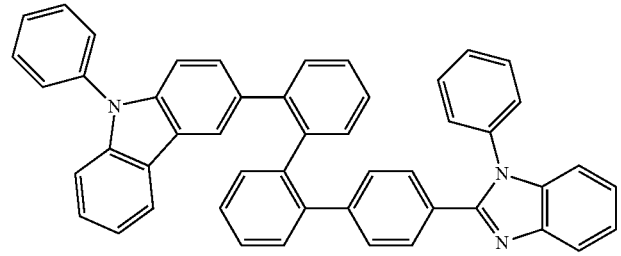

(Host-2)

9-phenyl-3-(4''-(1-phenyl-1H-benzo[d]imidazol-2-yl)-[1,1':2',1''-terphenyl]-2-yl)-9H-carbazole

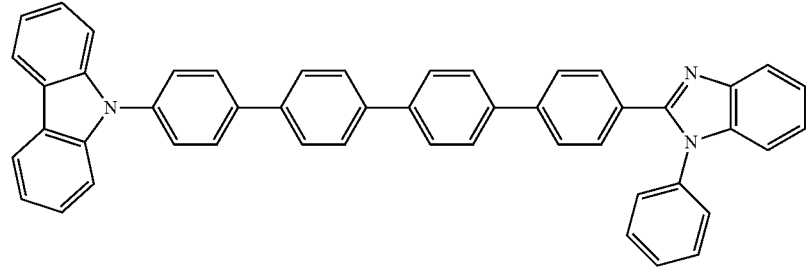

(Host-6)

9-(4'''-(1-phenyl-1H-benzo[d]imidazol-2-yl)-[1,1':4',1'':4'',1'''-quaterphenyl]-4-yl)-9H-carbazole

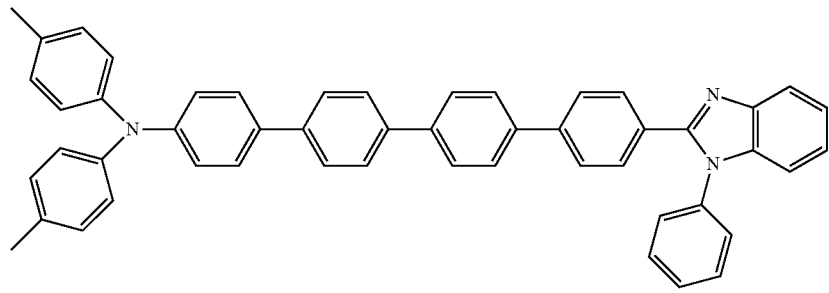

(Host-7)

4'''-(1-phenyl-1H-benzo[d]imidazol-2-yl)-N,N-di-p-tolyl-[1,1':4', 1":4", 1'''-quarterphenyl]-4-amine

TABLE 1

| Compound | T₁ (eV) |
|---|---|
| HOST-1 | 2.36 |
| HOST-2 | 2.59 |
| HOST-6 | 2.38 |
| HOST-7 | 2.4 |

In some embodiments, a dopant of the fluorescent blue emissive layer may be any suitable compound that is a fluorescent blue emitter. Suitable compounds that may be useful as dopant materials for the fluorescent blue emissive layer may include, but are not limited to, any compound described in one of the following documents: U.S. Provisional Application No. 61/695,716, filed Aug. 31, 2012, which is incorporated by reference for all disclosure related to chemical compounds; U.S. patent application Ser. No. 13/232,837, filed Sep. 14, 2011, and published as US 20120179089, which is incorporated by reference for all disclosure related to chemical compounds; and U.S. Provisional Application No. 61/735,488, filed Dec. 10, 2012, which is incorporated by reference for all disclosure related to chemical compounds. In some embodiments, the dopant may be any of:

(BE-1)

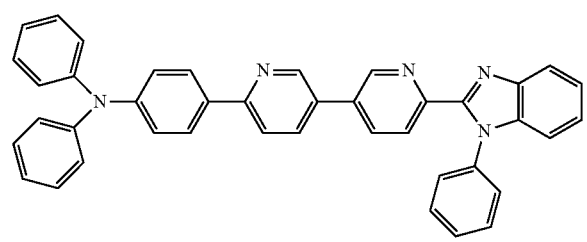

N,N-diphenyl-4-(6'-(1-phenyl)-1H-benzo[d]imidazol-2-yl)-[3,3'-bipyridin]-6-yl)aniline

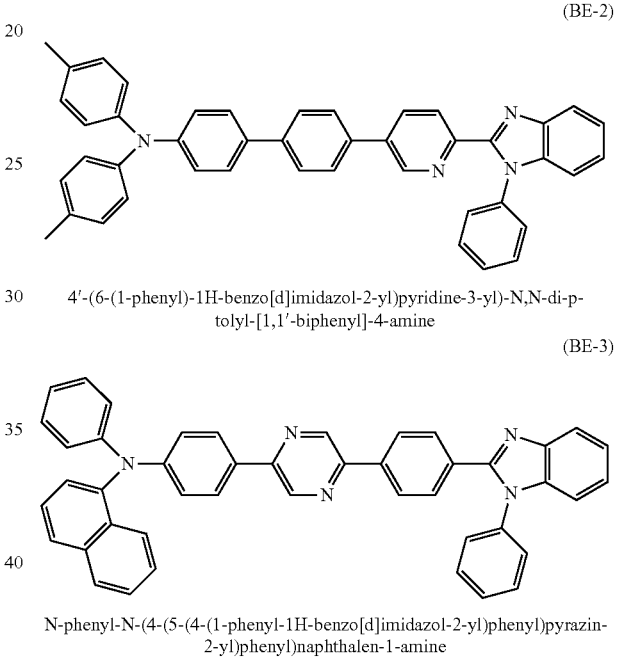

(BE-2)

4'-(6-(1-phenyl)-1H-benzo[d]imidazol-2-yl)pyridine-3-yl)-N,N-di-p-tolyl-[1,1'-biphenyl]-4-amine (BE-3)

N-phenyl-N-(4-(5-(4-(1-phenyl-1H-benzo[d]imidazol-2-yl)phenyl)pyrazin-2-yl)phenyl)naphthalen-1-amine In some embodiments, the dopant concentration in the fluorescent blue emissive layer is about 0.01 to about 10% by weight. In some embodiments, the dopant concentration in the fluorescent blue emissive layer is about 2.0 to about 15% by weight, about 4% to about 8% by weight, is about 5% by weight, or about 6% by weight. In another embodiment, the fluorescent blue emitter comprises BE-3.

In another embodiment, a fluorescent blue emissive layer has a thickness of at least about 5 nm, at least about 10 nm, up to about 20 nm, up to about 25 nm, up to about 30 nm, up to about 40 nm, up to about 50 nm, or any thickness in a range bounded by, or between, any of these values. In another embodiment, the fluorescent blue emissive layer has a thickness of about 15 nm.

In some embodiments, the fluorescent blue emissive layer is the second thickest layer in the emissive construct. The intermediate thickness of the fluorescent blue emissive layer can allow a significant amount of blue light to be emitted, while also allowing a significant portion of the triplet excitons generated in the fluorescent blue emissive layer to be transferred to the phosphorescent red emissive layer, thus reducing loss of efficiency.

A phosphorescent red emissive layer emits red light, such as light that has an emissive peak, or an average emission, of about 590 nm to about 750 nm, by phosphorescence.

A phosphorescent red emissive layer may emit light of a lower wavelength than the fluorescent blue emissive layer, the phosphorescent green emissive layer, and the phosphorescent yellow emissive layer. In some embodiments the phosphorescent red emissive layer will have a lower $T_1$ energy than the fluorescent blue emissive layer, the phosphorescent green emissive layer, and the phosphorescent yellow emissive layer.

An advantage of having a phosphorescent red emissive layer contacting the fluorescent blue emissive layer is that the low energy $T_1$ of the phosphorescent red emissive layer can allow it to be an effective triplet energy trap for the fluorescent blue emissive layer. This can encourage efficient triplet energy transfer to the phosphorescent red emissive layer, thus increasing phosphorescent efficiency for the emissive construct.

In some embodiments, the phosphorescent red emissive layer comprises a host and at least one phosphorescent red light-emitting dopant. Suitable hosts include, but are not limited to those described in co-pending application U.S. Patent Publication No. 2011/0140093 (Ser. No. 13/033,473, filed Feb. 23, 2011); which is incorporated by reference for their description of chemical compounds. In some embodiments, the host for the red emissive layer may be Host-1.

In another embodiment, the phosphorescent red light-emitting dopant may be any of the following:

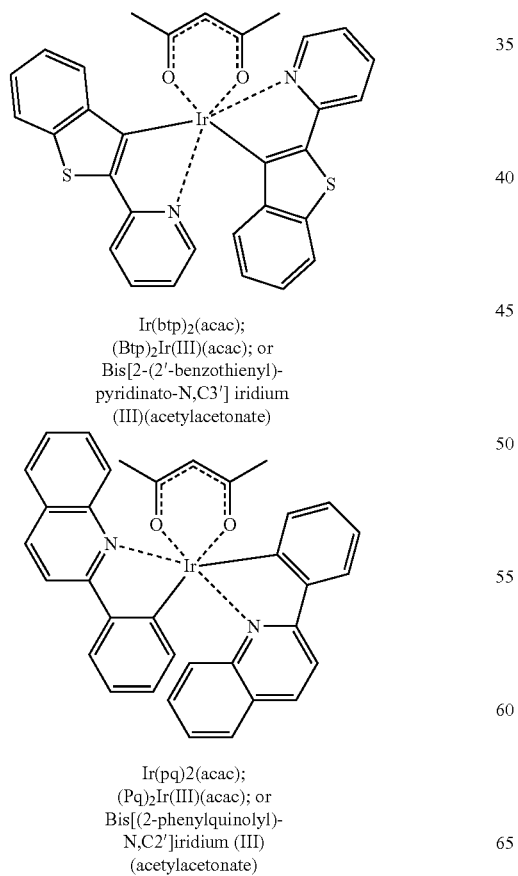

Ir(btp)2(acac);
(Btp)2Ir(III)(acac); or
Bis[2-(2'-benzothienyl)-
pyridinato-N,C3'] iridium
(III)(acetylacetonate)

Ir(pq)2(acac);
(Pq)2Ir(III)(acac); or
Bis[(2-phenylquinolyl)-
N,C2']iridium (III)
(acetylacetonate)

-continued

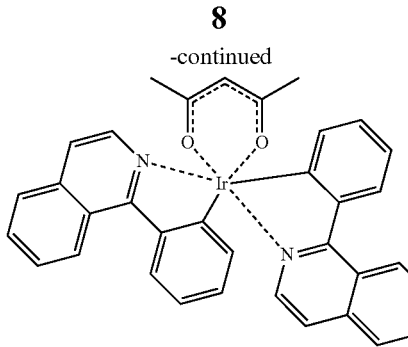

Ir(piq)2(acac);
(Piq)2Ir(III)(acac); or
Bis[(1-
phenylisoquinolinato)-
N,C2'] iridium (III)
(acetylacetonate)

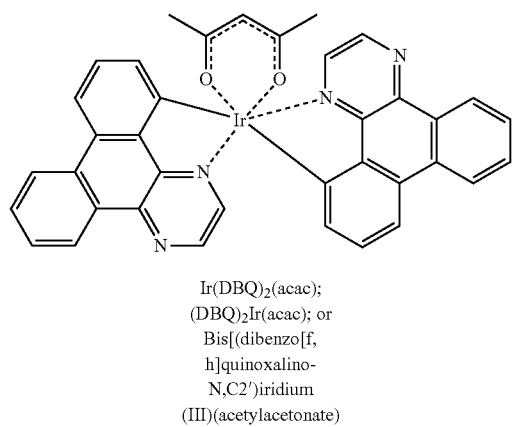

Ir(DBQ)2(acac);
(DBQ)2Ir(acac); or
Bis[(dibenzo[f,
h]quinoxalino-
N,C2')iridium
(III)(acetylacetonate)

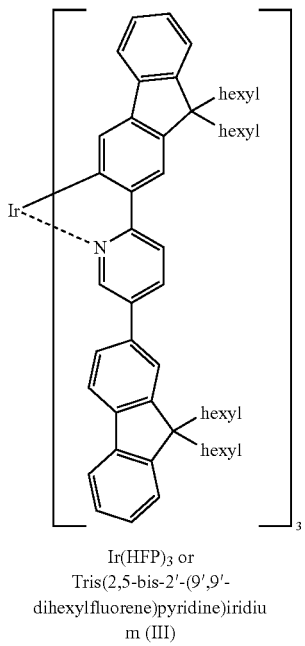

Ir(HFP)3 or
Tris(2,5-bis-2'-(9',9'-
dihexylfluorene)pyridine)iridiu
m (III)

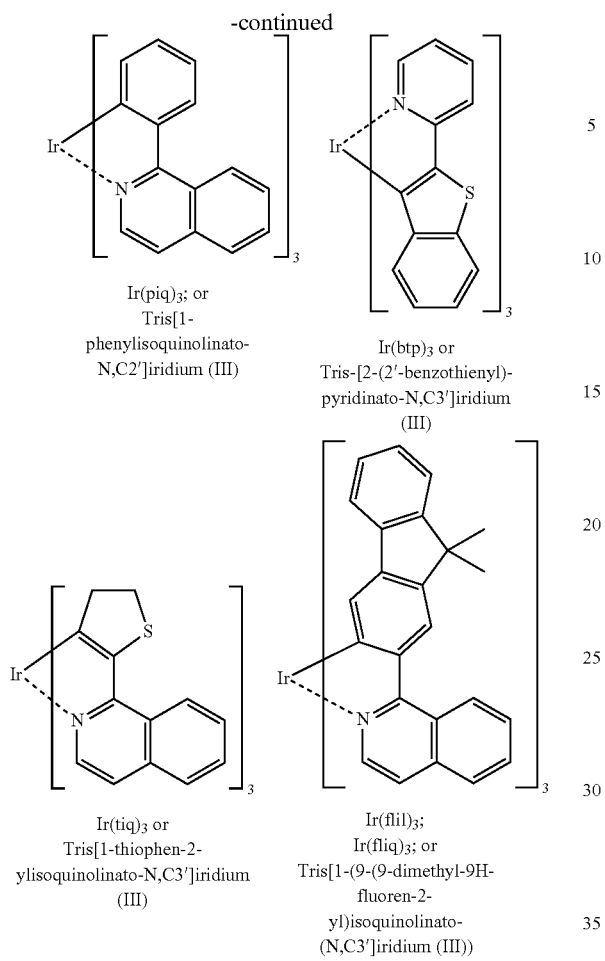

Ir(piq)₃; or
Tris[1-phenylisoquinolinato-N,C2']iridium (III)

Ir(btp)₃ or
Tris-[2-(2'-benzothienyl)-pyridinato-N,C3']iridium (III)

Ir(tiq)₃ or
Tris[1-thiophen-2-ylisoquinolinato-N,C3']iridium (III)

Ir(flil)₃;
Ir(fliq)₃; or
Tris[1-(9-(9-dimethyl-9H-fluoren-2-yl)isoquinolinato-(N,C3']iridium (III))

A phosphorescent red emissive layer may be doped or undoped. If the phosphorescent red emissive layer is doped, any suitable dopant concentration may be used, such as, about 2% to about 20%, about 5% to about 15%, or about 10% by weight.

The phosphorescent red emissive layer may have any suitable thickness. In some embodiments, the phosphorescent red emissive layer has a thickness of about 0.1 nm to about 10 nm, about 0.2 nm to about 5 nm, about 0.5 nm to about 3 nm, or about 1 nm.

A phosphorescent green emissive layer emits green light, such as light that has an emissive peak, or an average emission, of about 500 nm to about 570 nm, by phosphorescence.

A phosphorescent green emissive layer may emit light of a lower wavelength than the fluorescent blue emissive layer, and a higher wavelength than the phosphorescent red emissive layer and the phosphorescent yellow emissive layer. In some embodiments the phosphorescent green emissive layer will have a lower $T_1$ energy than the fluorescent blue emissive layer, and a higher $T_1$ energy than the phosphorescent red emissive layer and the phosphorescent yellow emissive layer.

If the HOMO of the host for a green phosphorescent emissive layer is lower than that of the host for the blue fluorescent emissive layer the host for the phosphorescent green emissive layer can function to partially block holes. If the blue fluorescent emissive layer and the red phosphorescent emissive layer are between the anode and the green phosphorescent emissive layer, increasing the thickness of the green phosphorecent emissive layer can confine a greater number of holes in the red phosphorescent emissive layer, and thus increase exciton formation in the red phoshorescent emissive layer. If the red phosphorescent emissive layer is very thin, the number of holes, and the number of excitons formed, in the florescent blue emissive layer can also increase as the thickness of the green phosphorescent emissive layer is increased. Thus, both red and blue emission can be enhanced with by increasing the thickness of the green emissive layer. In some embodiments, the phosphorescent green emissive layer comprises a host and at least one phosphorescent green light-emitting dopant. Suitable hosts in the green emissive layer include, but are not limited to, those described in the following documents: U.S. Provisional Application, app. No. 61/735,478, filed on Dec. 10, 2012, and U.S. patent application Ser. No. 14/102,138, filed Dec. 10, 2013, which are incorporated by reference herein for all disclosure related to chemical compounds. In another embodiment, the host may be Host-2. In another embodiment, the phosphorescent green emissive layer has a host with a $T_1$ value which may be higher than 2.5 eV. In another embodiment, the phosphorescent green light-emitting dopant may be any of the following:

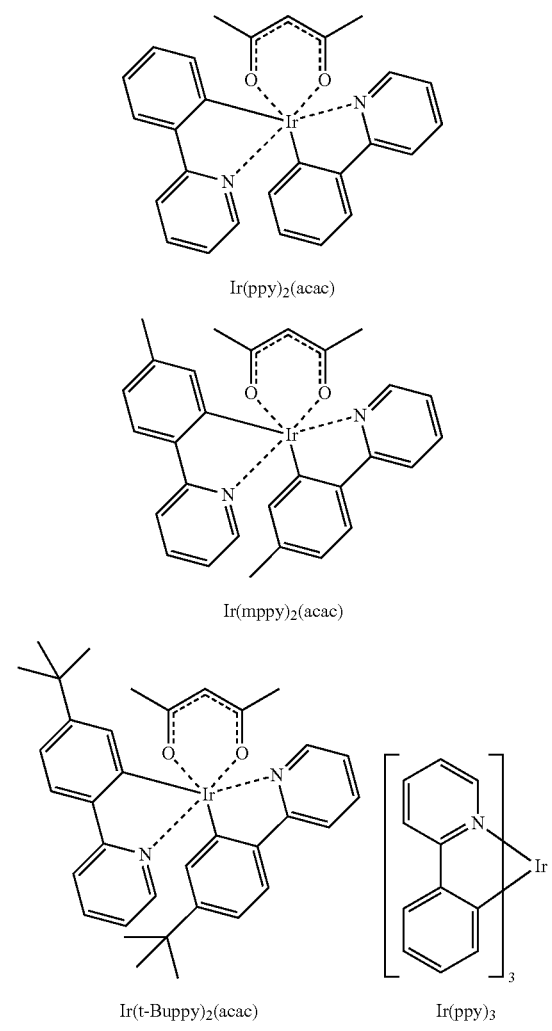

Ir(ppy)₂(acac)

Ir(mppy)₂(acac)

Ir(t-Buppy)₂(acac)

Ir(ppy)₃

-continued

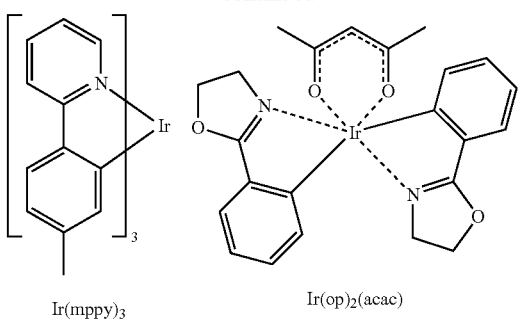

Ir(mppy)₃

Ir(op)₂(acac)

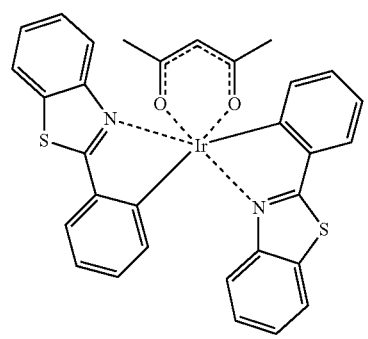

(bt)₂Ir(III)(acac)
bis[2-phenyl
benzothiazolato-
N,C2'] iridium (III)
(acetylacetonate)

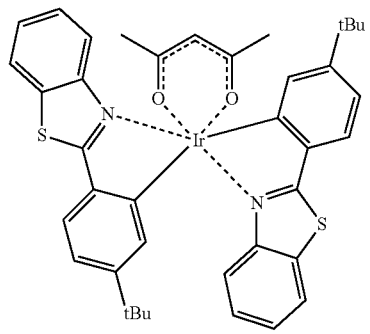

(t-bt)₂Ir(III)(acac)
bis[2-(4-tert-
butylphenyl)
benzothiazolato-N,C2']
iridium (III)
(acetylacetonate)

-continued

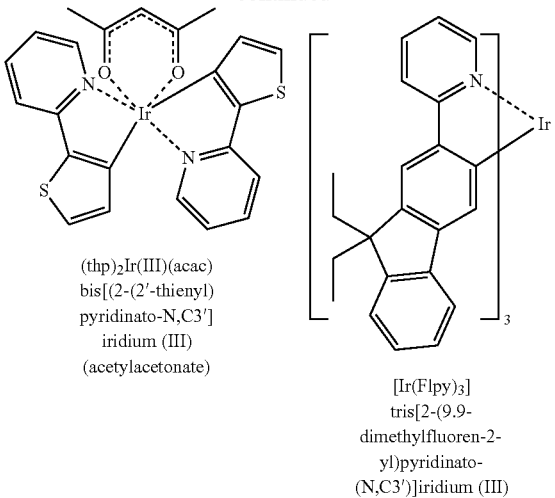

(thp)₂Ir(III)(acac)
bis[(2-(2'-thienyl)
pyridinato-N,C3']
iridium (III)
(acetylacetonate)

[Ir(Flpy)₃]
tris[2-(9,9-
dimethylfluoren-2-
yl)pyridinato-
(N,C3')]iridium (III)

(Cz-CF₃)Ir(III)(acac)
Bis[5-trifluoromethyl-2-[3-(N-
phenylcarbzolyl)pyridinato-
N(C2']iridium(III)acetylacetonate)

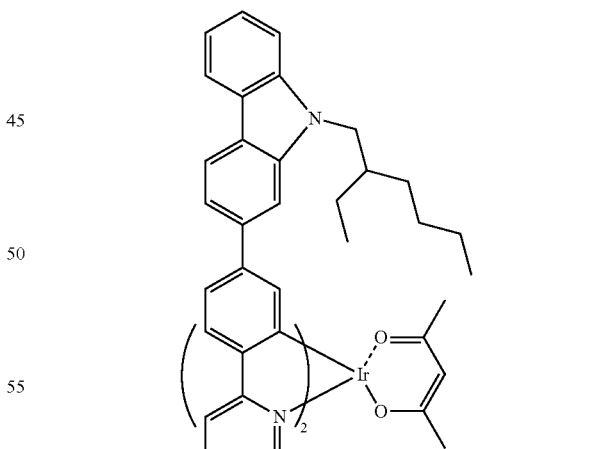

(2-
PhPyCz)₂Ir(III)(acac)

A phosphorescent green emissive layer may be doped or undoped. If the green phosphorescent emissive layer is doped, any suitable dopant concentration may be used. For example, the dopant concentration in the green phosphorescent emissive layer may be about 2 to 20%, about 2 to about 15%, or about 6% by weight.

A green phosphorescent emissive layer can have any suitable thickness. In some embodiments, a green phosphorescent emissive layer has a thickness of about 1 nm to about 10 nm, about 3 nm to about 5 nm, about 3 nm to about 4 nm, or about 3.5 nm.

A phosphorescent yellow emissive layer emits yellow light, such as light has an emissive peak, or an average wavelength, of about 570 nm to about 590 nm, by phosphorescence.

A phosphorescent yellow emissive layer may emit light of a lower wavelength than the fluorescent blue emissive layer and the phosphorescent green emissive layer, and a higher wavelength than the phosphorescent red emissive layer. In some embodiments the phosphorescent yellow emissive layer will have a lower $T_1$ energy than the fluorescent blue emissive layer and the phosphorescent green emissive layer, and a higher $T_1$ energy than the phosphorescent red emissive layer.

In some embodiments, a phosphorescent yellow emissive layer comprises a host and at least one phosphorescent yellow light-emitting dopant. Suitable hosts include, but are not limited to those described in co-pending application U.S. Patent Publication No. 2011/0140093 (Ser. No. 13/033,473, filed Feb. 23, 2011). In another embodiment, the yellow host comprises Host-1. In some embodiments, the phosphorescent yellow light-emitting dopant may be any of the following:

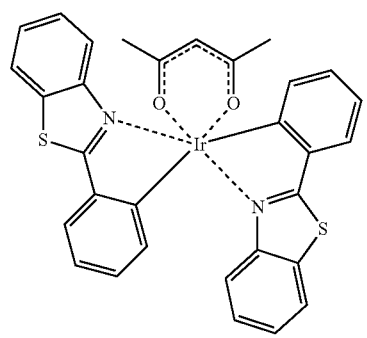

(bt)$_2$Ir(III)(acac)
bis[2-phenylbenzothiazolato-N,C2'] iridium (III)(acetylacetonate)

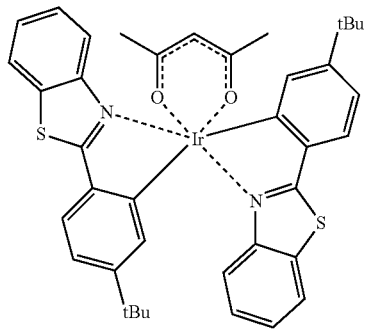

(t-bt)$_2$Ir(III)(acac)
bis[2-(4-tert-butylphenyl)benzothiazolato-N,C2']iridium(III) (acetylacetonate)

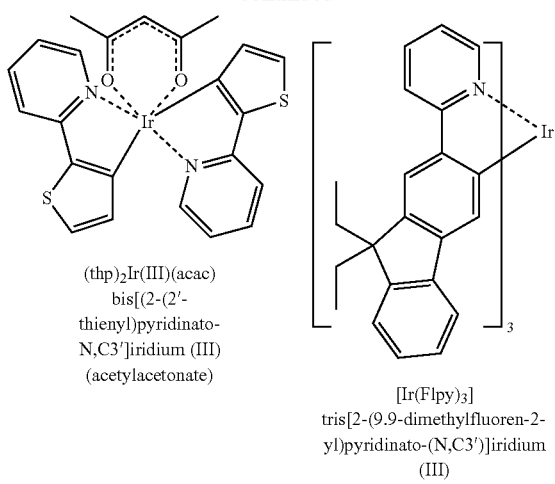

(thp)$_2$Ir(III)(acac)
bis[(2-(2'-thienyl)pyridinato-N,C3']iridium (III) (acetylacetonate)

[Ir(Flpy)$_3$]
tris[2-(9,9-dimethylfluoren-2-yl)pyridinato-(N,C3')]iridium (III)

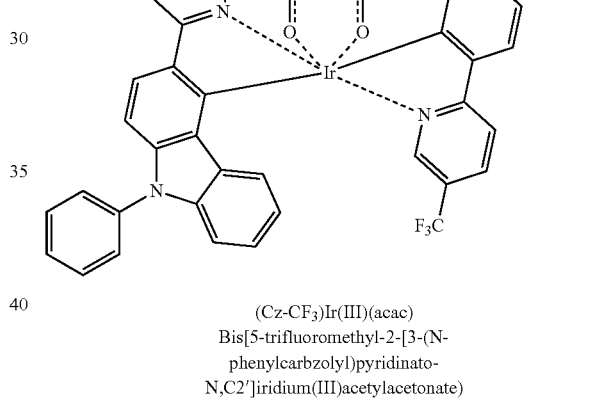

(Cz-CF$_3$)Ir(III)(acac)
Bis[5-trifluoromethyl-2-[3-(N-phenylcarbzolyl)pyridinato-N,C2']iridium(III)acetylacetonate)

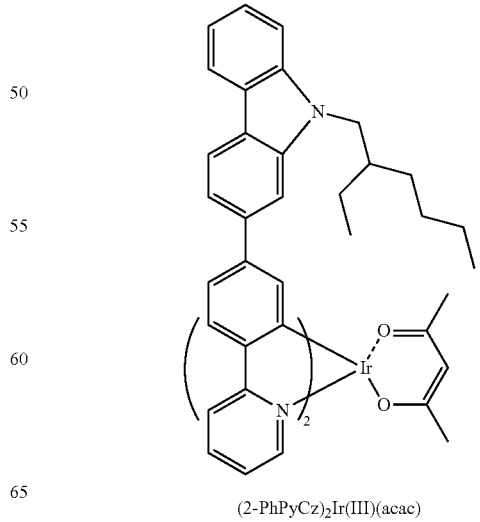

(2-PhPyCz)$_2$Ir(III)(acac)

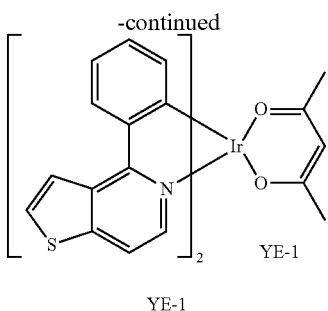

YE-1

A phosphorescent yellow emissive layer may be doped or undoped. If a phosphorescent yellow emissive layer is doped, any suitable dopant amount of phosphorescent yellow light-emitting dopant may be used, such as about 2% to about 20%, about 2% to about 10%, about 4% to about 8%, about 5% to about 7%, or about 6% by weight.

A phosphorescent yellow emissive layer may have any suitable thickness, such as about 5 nm to 50 nm, about 20 nm to about 50 nm, or about 30 nm.

In some embodiments, a phosphorescent yellow emissive layer may be the thickest layer in the emissive construct. This can allow a significant amount of the triplet excitons to be converted to light.

In some embodiments, the combined thickness of the fluorescent blue emissive layer and the phosphorescent yellow emissive layer are the majority of the thickness of the emissive construct, such as at least about 70%, at least about 80%, at least about 90%, or about 90% to about 95%, of the thickness of the emissive construct.

In another embodiment, the host for the fluorescent blue emissive layer, phosphorescent red emissive layer, and the phosphorescent yellow emissive layer, comprise the same host. In another embodiment, the host is an ambipolar host. Suitable hosts include, but are not limited to those described in co-pending applications U.S. Patent Publication No. 2011/0140093 (Ser. No. 13/033,473, filed Feb. 23, 2011); U.S. Patent Publication No. 2011/0251401 (Ser. No. 13/166, 246, filed Jun. 11, 2011), U.S. Patent Publication No. 2010/0326526 (Ser. No. 12/825,953, filed Jun. 29, 2010); which are incorporated by reference herein for all disclosure related to chemical compounds. In another embodiment, the ambipolar host for the fluorescent blue emissive layer, phosphorescent red emissive layer, and the phosphorescent yellow emissive layer may be any of the following:

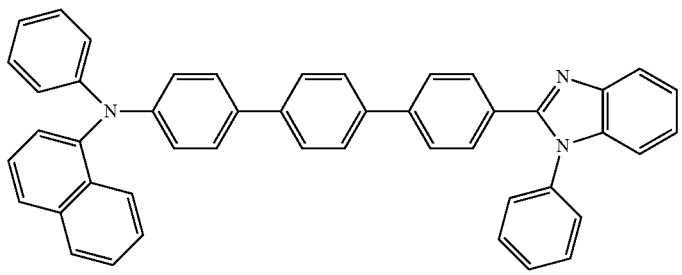

Host-3

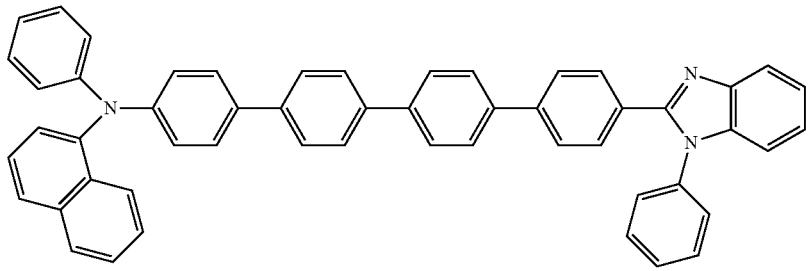

Host-1

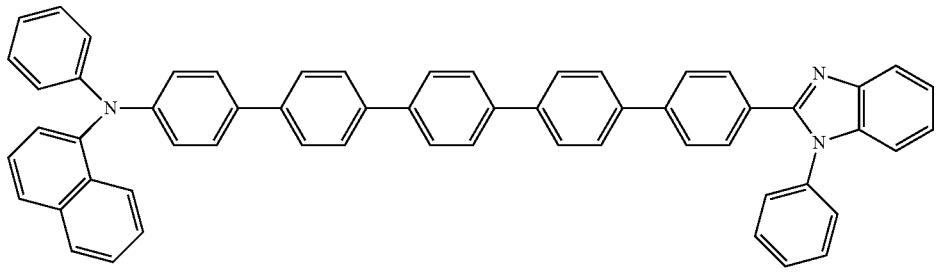

Host-4

In another embodiment, the ambipolar host for the fluorescent blue emissive layer, phosphorescent red emissive layer, and the phosphorescent yellow emissive layer comprises Host-1.

In another embodiment, a white emitting OLED device is provided comprising: a cathode; an anode; and the emissive constructs described above being disposed between the anode and cathode.

In another embodiment, a white light emitting OLED device is provided comprising in sequence from bottom to top, a substrate; an insulating layer coated on top of the substrate; a reflective and opaque anode above the insulating layer; a hole injection layer above the anode; a hole transport layer above the hole injection layer; the emissive construct described above; an electron transporting layer above the emissive construct; an electron injection layer above the electron transporting layer; a semi transparent or transparent cathode above the electron transport layer; a light emission enhancement layer, for example a capping layer, above the cathode; and a light scattering layer, for example a color mixing layer, disposed above the light emission enhancement layer.

Suitable light scattering materials include, but are not limited to those described in co-pending applications U.S. patent application Ser. No. 13/672,394, filed Nov. 8, 2012; U.S. patent application Ser. No. 13/410,812, filed Mar. 2, 2012; and U.S. Provisional Application No. 61/696,085, filed Aug. 31, 2012, which are incorporated by reference herein for all disclosure related to light scattering or nanostructured compounds. In another embodiment, the light scattering layer may comprise

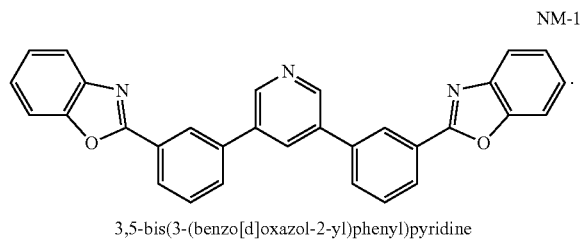 [SMILES: c1cc(-c2cncc(-c3cccc(-c4nc5ccccc5o4)c3)c2)cc(-c2nc3ccccc3o2)c1 ; "."]

3,5-bis(3-(benzo[d]oxazol-2-yl)phenyl)pyridine

An OLED may further comprise a light outcoupling lens. In some embodiments, the light outcoupling lens may comprise epoxy material. In some embodiments, the epoxy material may be disposed upon the light scattering materials described above. In some embodiments, the epoxy material may be substantially hemispherical.

In another embodiment, a method for color tuning a white light emitting hybrid OLED device which emits a more blue and/or more red light is described comprising inserting the emissive construct described above between an anode and a cathode; and thickening the green emissive layer a sufficient amount to provide the desired white color output, e.g., CRI values. In another embodiment, the thickening of the green emissive layer may be a sufficient amount to tune the emission spectrum of the emissive layer. In some embodiments, a green emissive layer thickness may be increased by of at least about 10% resulting in an increase in blue emissions around 10% or more. In some embodiments, a green emissive layer thickness may be increased by about 10% or more resulting in a decrease in red emissions of at least about 10% or more.

In another embodiment, a method for color tuning a white light emitting hybrid OLED device to emit a warmer (more red/orange light) light is described comprising: inserting the emissive construct described above between an anode and a cathode; and thinning the green emissive layer a sufficient distance to provide the desired white color output, e.g., CRI values. I.

An anode, e.g. first electrode 30 or second electrode 120 (depending upon how the device is configured), may be a layer comprising a conventional material such as a metal, a mixed metal, an alloy, a metal oxide or a mixed-metal oxide, a conductive polymer, and/or an inorganic material such as a carbon nanotube (CNT). Examples of suitable metals include the Group 1 metals, the metals in Groups 4, 5, or 6, and the Group 8, 9, and 10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (Jun. 11, 1992). In some embodiments, the anode layer may have a thickness in the range of about 1 nm to about 1000 nm.

A cathode, e.g. first electrode 30 or second electrode 120 (depending upon how the device is configured), may be a layer including a material having a lower work function than the anode layer. Examples of suitable materials for the cathode layer include alkali metals of Group 1, Group 2 metals, Group 12 metals, including rare earth elements, lanthanides and actinides, materials such as aluminum, indium, calcium, barium, samarium and magnesium, and combinations thereof. Li-containing organometallic compounds, LiF, and Li$_2$O may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer may have a thickness in the range of about 1 nm to about 1000 nm.

If present, a hole-transport layer, e.g. hole-transport layer 60, may be disposed between the anode and the emissive construct or an emissive layer. A hole-transport layer may comprise at least one hole-transport material. Hole-transport materials may include, but are not limited to, an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(p-phenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-bis(4-bis(4-methylphenyl) aminophenyl) cyclohexane; 2,9-dimethyl-4,7-diphenyl-1,10-phenanthroline; 3,5-bis(4-tert-butyl-phenyl)-4-phenyl[1,2,4]triazole; 3,4,5-triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); bis[4-(p,p'-ditolyl-amino)phenyl]diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; or the like.

If present, an electron-transport layer, e.g. electron-transport layer 80, may be disposed between the cathode and the emissive construct or an emissive layer. Examples of electron-transport materials may include, but are not limited to, 2-(4-biphenylyl)-5-(4-tert-butylphenyl)-1,3,4-oxadiazole (PBD); 1,3-bis(N,N-tert-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1, 2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

The thickness of an electron-transport layer may vary. For example, some electron-transport layers may have a thickness of about 5 nm to about 200 nm, about 10 nm to about 80 nm, or about 20 nm to about 40 nm.

If desired, additional layers may be included in a light-emitting device, such as an electron injecting layer (EIL), a hole-blocking layer (HBL), an exciton-blocking layer (EBL), a hole-injecting layer (HIL), etc. In addition to separate layers, some of these materials may be combined into a single layer.

If present, an electron-injecting layer, e.g. electron-injecting layer 90, may be between a cathode and an emissive construct or emissive layer. Examples of suitable material(s) that may be included in the electron injecting layer include but are not limited to, an optionally substituted compound selected from the following: aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato)zinc. In one embodiment, the electron injecting layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If present, a hole-blocking layer may be between a cathode and a emissive construct or emissive layer. Examples of suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, a light-emitting device may include an exciton-blocking layer. In an embodiment, the band gap of the material(s) that comprise exciton-blocking layer is large enough to substantially prevent the diffusion of excitons. A number of suitable exciton-blocking materials that may be included in the exciton-blocking layer are known to those skilled in the art. Examples of material(s) that may compose an exciton-blocking layer include an optionally substituted compound selected from the following: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

If present, a hole-injecting layer, e.g. hole-injecting layer 40, may be between an emissive construct or emissive layer and the anode. Examples of suitable hole-injecting material(s) include, but are not limited to, an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino) triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), and a phthalocyanine metal complex derivative such as phthalocyanine copper.

A capping layer, which can be a layer on top of the cathode, may be any material having the function of light output enhancement. Examples of capping layer materials may be similar to those of enhancement layers, such a transparent materials including organic small molecule materials such as NPB, TPBI, Alq3; metal oxides such as MoO$_3$, WO$_3$, SnO$_2$ and SnO; wide band gap semiconductor compounds; etc. Additional examples include enhancement layers and/or porous films as described in US Patent Application Publication 20120223635, entitled, "POROUS FILMS FOR USE IN LIGHT-EMITTING DEVICES," which is herein incorporated by reference in its entirety. In some embodiments, the capping layer comprises 4,4'-bis[N-(naphthyl)-N-phenyl-amino]biphenyl (NPB).

A capping layer may be of any thickness suitable for enhancing light output. In some embodiments, the capping layer has a thickness of about 10 nm to about 1000 nm, about 50 nm to about 200 nm, or about 100 nm.

If present, a light scattering layer, such as light scattering layer 130, e.g. nanostructured material, may be disposed on: the anode, the cathode, a transparent layer disposed between the anode and the porous film, or a transparent layer disposed between the cathode and the porous film. The nanostructured materials may comprise any nanostructure material described in the following documents: U.S. Patent Publication No. 2012/0223635 (Ser. No. 13/410,812, filed Mar. 2, 2012, U.S. patent application Ser. No. 13/672,394, filed Nov. 8, 2012 and U.S. Provisional Application Ser. No. 61/696,085, filed Aug. 31, 2012, which is incorporated by reference for their description of appropriate nanostructured materials.

In some embodiments, a light-scattering layer may comprise 3,5-bis(3-(benzo[d]oxazol-2-yl)phenyl)pyridine.

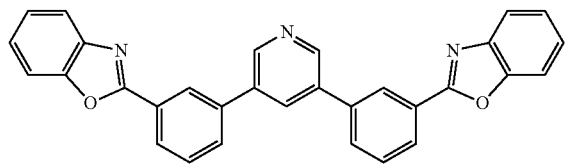

3,5-bis(3-(benzo[d]oxazol-2-yl)phenyl)pyridine

Light-emitting devices comprising a subject compound may be fabricated using techniques known in the art, as informed by the guidance provided herein. For example, a glass substrate may be coated with a high work functioning metal such as ITO which may act as an anode. In another example, a glass substrate may be coated with a reflective metal such as Al which may act as an anode. After patterning the anode layer, a hole-injecting and/or hole-transport layer may be deposited on the anode in that order. Emissive layers may be deposited on the anode, the hole-transport layer, or the hole-injecting layer. An emissive layer may contain plural emissive compounds. An electron-transport layer and/or an electron-injecting layer may be deposited in that order on the emissive layer(s). The cathode layer, comprising a low work functioning metal (e.g., Mg:Ag), may then be deposited, e.g., by vapor deposition or sputtering. The device may also contain an exciton-blocking layer, an electron blocking layer, a hole blocking layer, or other layers that may be added to the device using suitable techniques.

Example 1

Device Fabrication

Device A-1 was prepared having a structure consistent with that depicted in FIG. 2. Pre-cleaned glass substrates covered with a 40 nm thick layer of SiN, were baked at about 200° C. for about 1 hour under ambient environment, then under UV-ozone treatment for about 30 minutes. The substrates were loaded into a deposition chamber. A reflective bottom anode, (100 nm Al layer) was deposited at a rate of about 2 Å/s. Molybdenum oxide ($MoO_3$, about 5 nm) was deposited as a hole-injecting layer at deposition rate of about 1 Å/s. Then a p-doping layer (10 nm), $MoO_3$ was co-deposited with 4,4'-bis[N-(naphthyl)-N-phenyl-amino]biphenyl (NPB) at 10% in volume ratio at the deposition rate of about 0.1 Å/s and about 1.0 Å/s for $MoO_3$ and NPB, respectively. A layer of NPB (about 30 nm) was then deposited as a hole-transport layer. A first fluorescent blue emissive layer (15 nm) was then deposited having a fluorescent blue emitter (BE-3) that was co-deposited with a host material (Host-1) at 6% in volume with the deposition rate of about 0.05 Å/s for BE-3 and about 1 Å/s for Host-1.

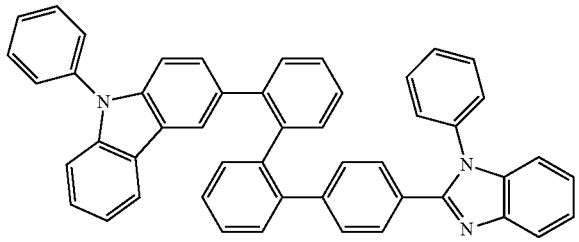

Host-2

Then the third phosphorescent layer (30 nm) was deposited by co-deposition of host (Host-1) with yellow emitter (YE-1) at a deposition rate of about 1 Å/s for Host-1 and about 0.05 Å/s for YE-1.

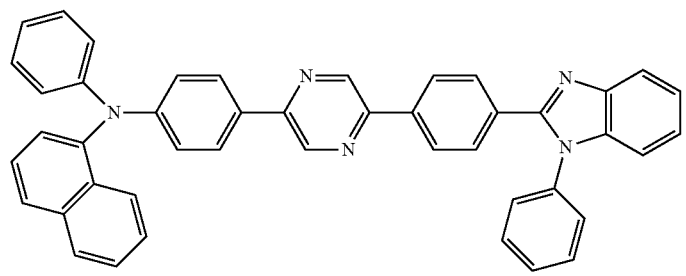

BE-3

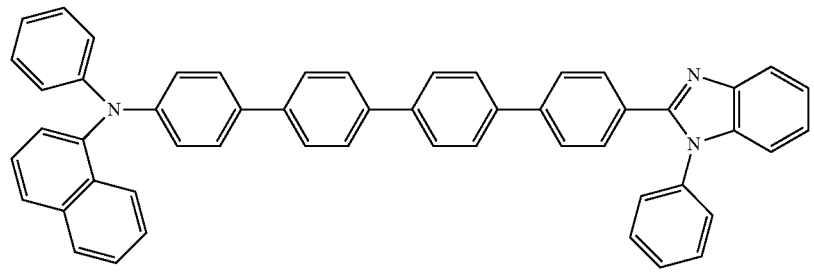

Host-1

Then the red phosphorescent emissive layer (1 nm) was deposited by co-deposition of host (Host-1) with red emitter ($Ir(piq)_2acac$, 10%) at the deposition rate of about 0.05 Å/s for Host-1, and about 0.005 Å/s for $Ir(pq)_2acac$. Then deposition of the green phosphorescent emissive layer (3.5 nm) of co-deposition of host (Host-2) with green emitter ($Ir(ppy)_3$, 6%) at the deposition rate of about 1 Å/s for Host-2, and about 0.06 Å/s for $Ir(ppy)_3$.

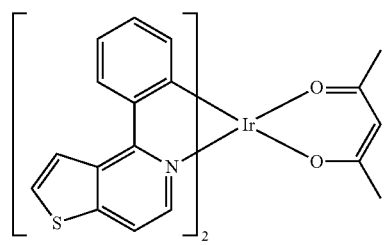

YE-1

-continued

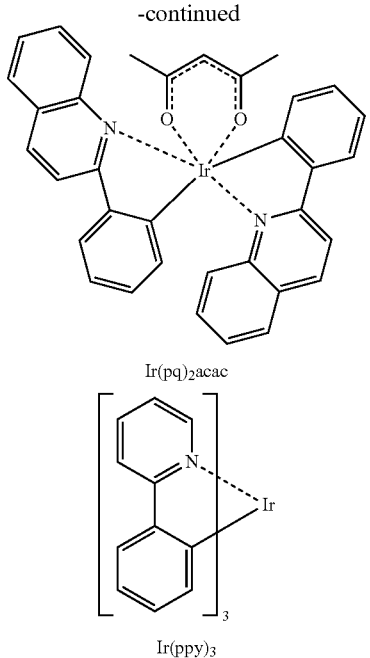

Ir(pq)₂acac

Ir(ppy)₃

The doping concentration of the red emitter was about 10 wt %, The doping concentration of the yellow emitter and the green emitter were about 6 wt % and about 6 wt %, respectively. Next, an electron transport layer (TPBI) of about 30 nm was deposited at the deposition rate of about 1 Å/s. The electron injection layer was then deposited as a thin layer of lithium fluoride (LiF, 1 nm thick, deposition rate 0.1 Å/s). A capping layer (NPB) was then deposited at a deposition rate of about 0.1 Å/s. A semi-transparent cathode (about 20 nm) was deposited by co-deposition of magnesium (Mg) and silver (Ag) at a ratio of about 1:3 by volume. Finally a light scattering layer of nanostructured material (3,5-bis(3-(benzo[d]oxazol-2-yl)phenyl)pyridine) was deposited on top of the light enhancement layer at deposition rate of about 2 Å/s for 600 nm. All the deposition was done at a base pressure of about $2\times10^{-7}$ torr. The device area was approximately 7.7 mm².

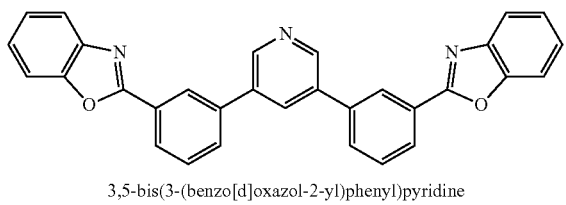 [SMILES: c1cc(-c2cncc(-c3cccc(-c4nc5ccccc5o4)c3)c2)cc(-c2nc3ccccc3o2)c1]

3,5-bis(3-(benzo[d]oxazol-2-yl)phenyl)pyridine

Additional devices (A2 [3.0 nm green layer] and A3 [2.5 nm green layer]) were constructed in the same manner, except that the thickness of the phosphorescent green emissive layer (the second phosphorescent layer) was varied as indicated in Table 2.

Additional devices (B-1, B-2, and B-3) were constructed in the same manner as above, except that an additional substantially hemispherical layer formed by a drop of epoxy substantially covering the entire surface of the device was disposed atop the nanostructure material (NM-1) layer.

Figure 4:
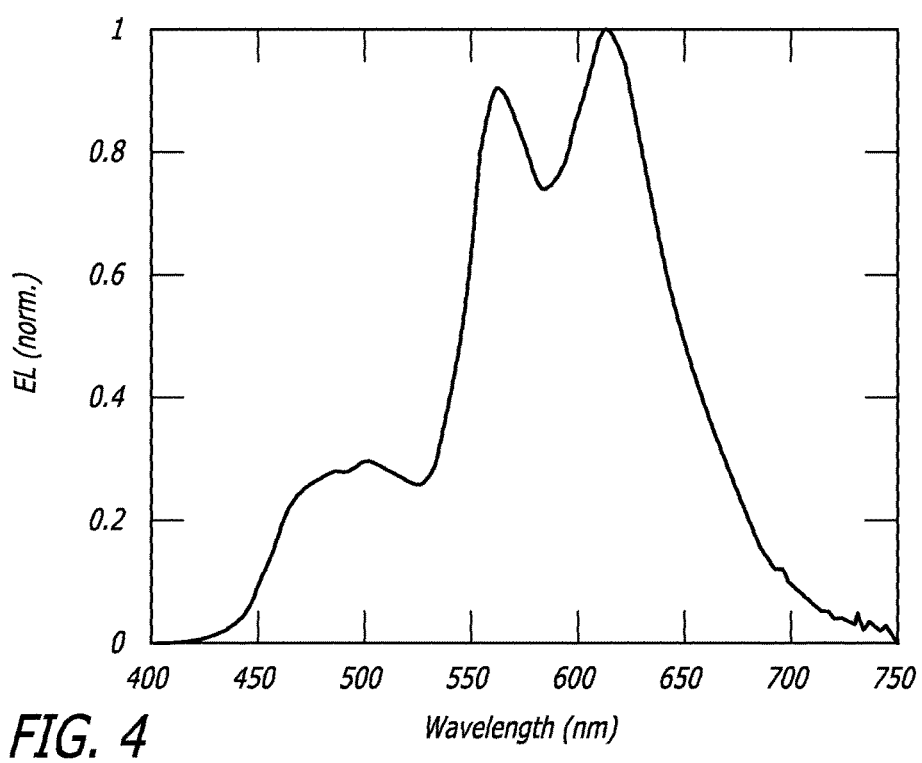
FIG. 4 is a plot of the EL spectrum of the Device A1 CRI(75), CIE(0.47, 0.44).
Figure 5:
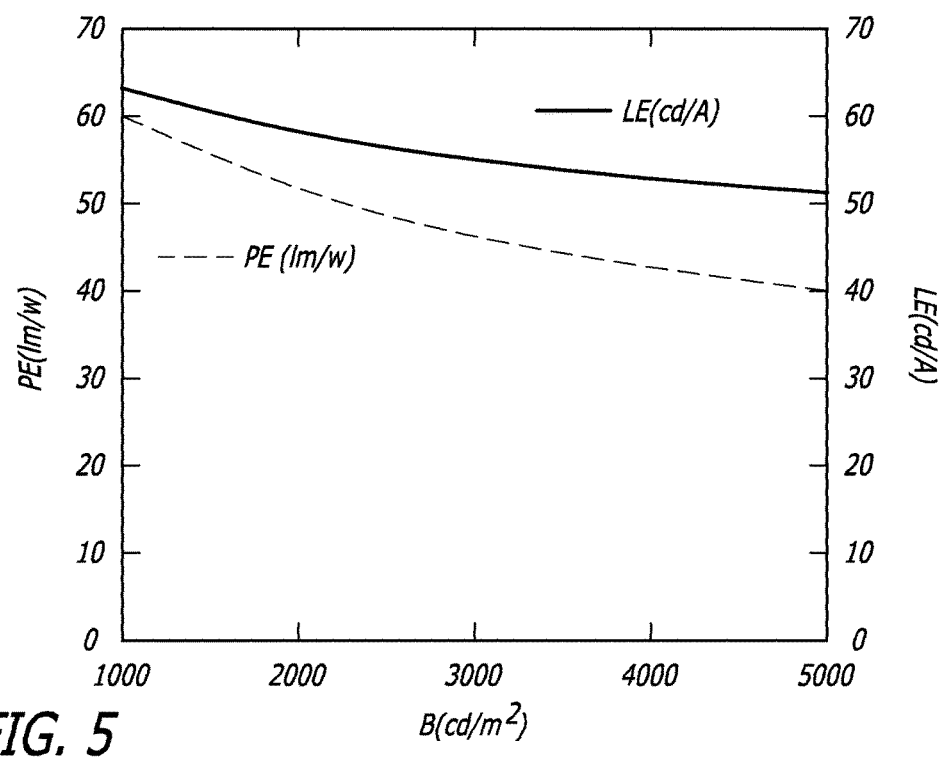
FIG. 5 is a plot of luminous efficiency and power efficiency against brightness (B) for Device A1.

FIG. 4 shows the electroluminescence (EL) spectrum (CRI 75, CIE(0.47, 0.44) of Device A1 at 1000 nit. FIG. 5 shows the device performance data, brightness dependence of the power efficiency and current efficiency of Device A1 at 1000 nit, 85 lm/w, 86 cd/A, and 32% EQE.

Figure 6:
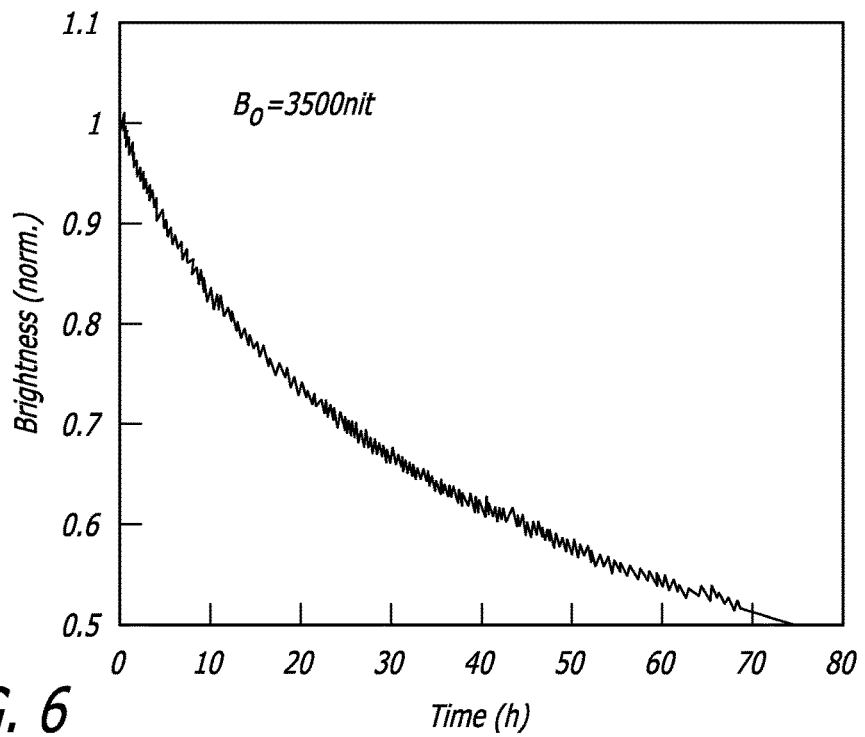
FIG. 6 is a plot of brightness over time for Device B1.
Figure 7:
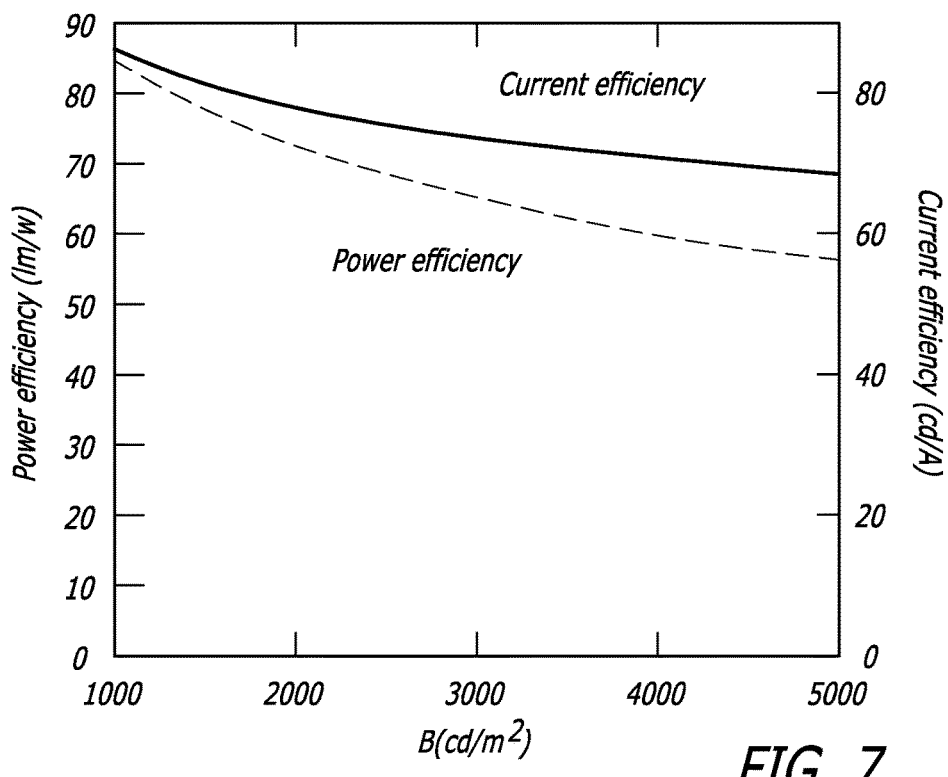
FIG. 7 is a plot of luminous efficiency and power efficiency against brightness (B) for Device B1.
Figure 8:
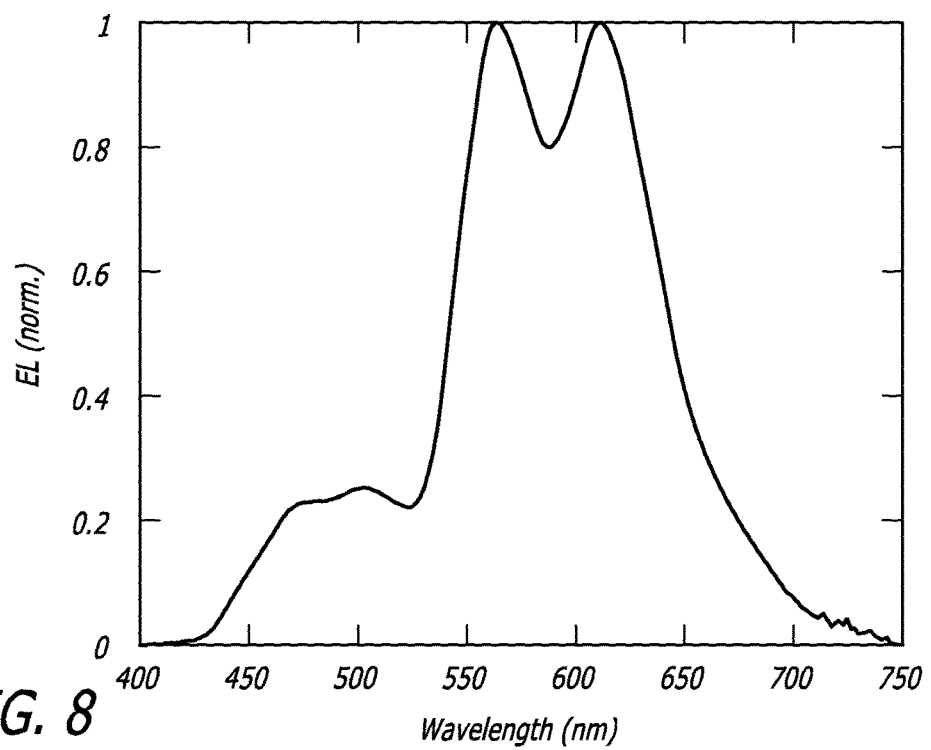
FIG. 8 is a plot of the EL spectrum of Device A2 (3.0 nm green layer) CRI(64), CIE(0.48, 0.45).

FIG. 6 shows the brightness over time of operation of Device B1 (Device A1 with outcoupling hemispherical layer) with an initial brightness of 3500 nit and an acceleration factor of 1.6, the device showed a LT70 of about 7500 h at 1000 nit. FIG. 7 shows the device performance data, brightness dependence of the power efficiency and current efficiency of Device B1 at 1000 nit, 85 lm/w, 86 cd/A, and 32% EQE.

Example 2

Figure 9:
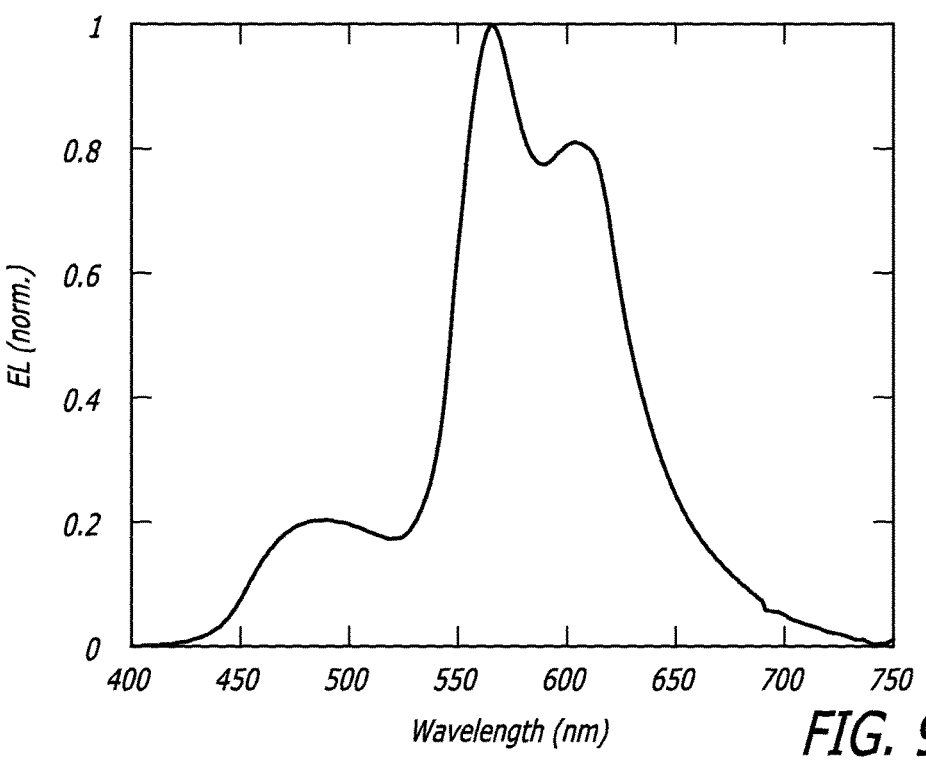
FIG. 9 is a plot of the EL spectrum of Device A3 (2.5 nm green layer)] CRI(55), CIE(0.56, 0.45).

Devices A3 and A2 were prepared using the same fabrication procedure as Device A1 (FIG. 3) except the thickness of the phosphorescent green emissive layer 16 was 2.5 nm, and 3.0 nm respectively. The EL spectrums of the devices were compared to discern the effect of the thickness of the green layer upon the EL spectrum. FIGS. 9 (CRI 55, CIE(0.56, 0.45)) and 8 (CRI 64, CIE(0.48, 0.45)) show the electroluminescence (EL) spectrum of Devices A3 and A2 respectively, at 1000 nit. A change in thickness of the green phosphorescent emissive layer 16 from 2.5 nm (Device A3), with a perceived peak blue emission of about 0.2 EL and a peak red emissive peak of about 0.8 EL (see FIG. 9), to a thickness of the green phosphorescent emissive layer 16 to about 3.5 nm (Device A1), resulted a perceived peak blue emission of about 0.3 EL and a peak red emissive peak of about 1.0 EL (see FIG. 4). The perceived changes in the peak emissions were about 0.2 (Device A3) to 0.3 EL (Device A1) for the blue emissive peak and about 0.8 (Device A3) to about 1.0 EL (Device A1) for the red emissive peak. The perceived changes in the CRI values were about 55 (Device A3) to 64 (Device A2) to 75 (Device A1).

The results at 1000 cd/m² are also summarized in Table 2.

TABLE 2

| Device | Device Configuration | LE (cd/A) | PE (lm/W) | EQE | CRI |
|---|---|---|---|---|---|
| Green EML 2.5 (Device A3) | Without Outcoupling lens | 66 | 67 | 22% | 55- |
| Green EML 3.0 (Device A2) | Without Outcoupling lens layer | 67 | 67 | 24% | 64- |
| Green EML 3.5 (Device A1) | Without Outcoupling lens layer | 62 | 60 | 25% | 75- |
| Green EML 2.5 (Device B3) | w/Outcoupling lens | 93 | 96 | 30% | |
| Green EML 3.0 (Device B2) | w/Outcoupling lens | 94 | 97 | 32% | |
| Green EML 3.5 (Device B1) | w/Outcoupling lens | 86 | 85 | 32% | |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. An emissive construct comprising:
  a fluorescent blue emissive layer,
  a phosphorescent red emissive layer contacting the fluorescent blue emissive layer;
  a phosphorescent green emissive layer, having a host and a dopant, wherein the host has a triplet energy ($T_1$) level that is at least about 2.2 eV, and contacting the phosphorescent red emissive layer; and
  a phosphorescent yellow emissive layer contacting the phosphorescent green emissive layer.

2. The emissive construct of claim 1, wherein the fluorescent blue emissive layer has an emissive peak of about 380 nm to about 500 nm.

3. The emissive construct of claim 1, wherein the phosphorescent red emissive layer has an emissive peak of about 590 nm to about 750 nm.

4. The emissive construct of claim 1, wherein the phosphorescent green emissive layer has an emissive peak of about 500 nm to about 570 nm.

5. The emissive construct of claim 1, wherein the phosphorescent yellow emissive layer has an emissive peak of about 570 nm to about 590 nm.

6. The emissive construct of claim 1, wherein the green emissive layer has a thickness of about 1 nm to about 10 nm.

7. The emissive construct of claim 1, wherein the green emissive layer has a thickness of about 3.5 nm.

8. The emissive construct of claim 1, the fluorescent blue emissive layer has a thickness of about 5 nm to about 50 nm.

9. The emissive construct of claim 8, wherein the fluorescent blue emissive layer has a thickness of about 15 nm.

10. The emissive construct of claim 1, wherein the phosphorescent red emissive layer has a thickness from about 0.1 nm to about 10 nm.

11. The emissive construct of claim 10, wherein the thickness of the phosphorescent red emissive layer is about 1 nm, and the phosphorescent red emissive layer comprises about 10% by weight of the dopant.

12. The emissive construct of claim 1, wherein the phosphorescent yellow emissive layer has a thickness of about 5 nm to about 50 nm.

13. The emissive construct of claim 12, wherein the phosphorescent yellow emissive layer has a thickness of about 30 nm.

14. The emissive construct of claim 1, wherein the fluorescent blue emissive layer comprises a host and a dopant.

15. The emissive construct of claim 14, wherein the host is

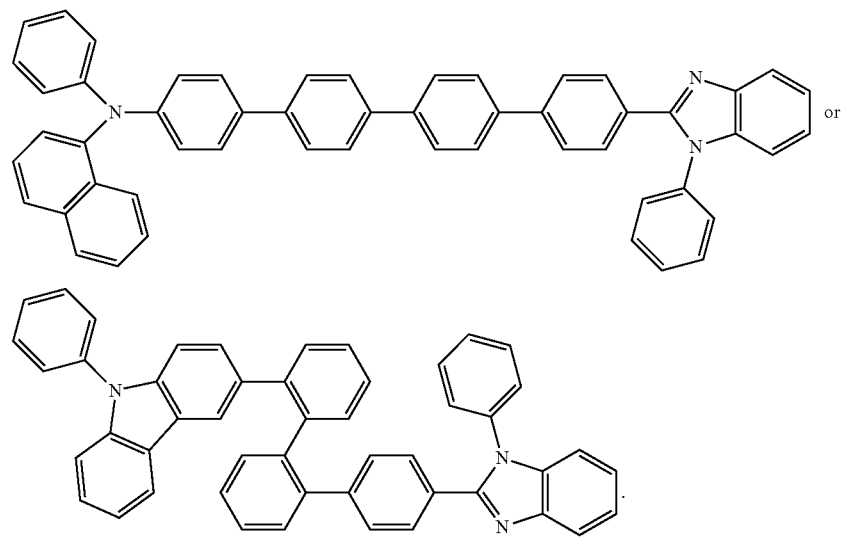

16. The emissive construct of claim 14, wherein the fluorescent blue emissive layer contains about 6% by weight of the dopant.

17. The emissive construct of claim 1, wherein the fluorescent blue emissive layer, the phosphorescent red emissive layer, and the phosphorescent yellow emissive layer comprise the same host.

18. The emissive construct of claim 17, wherein the host for the fluorescent blue emissive layer, the phosphorescent red emissive layer, and the phosphorescent yellow emissive layer is:

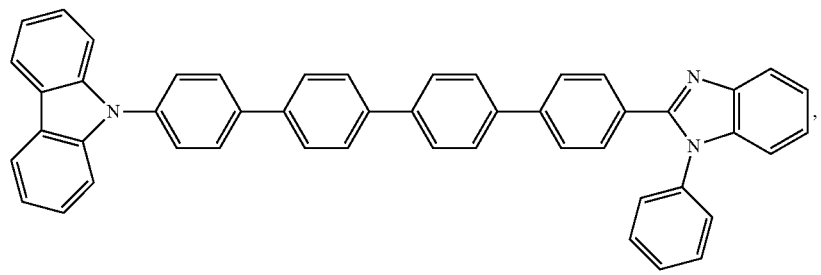

,

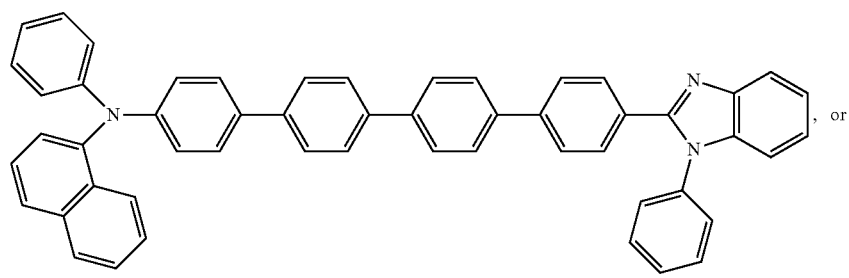

, or

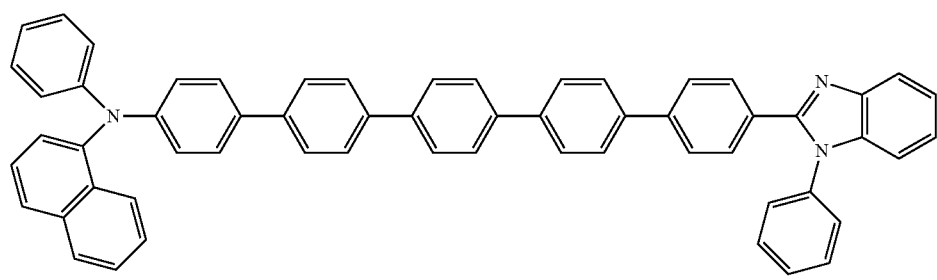

.

19. The emissive construct of claim 18, wherein the host for fluorescent blue emissive layer, the phosphorescent red emissive layer, and the phosphorescent yellow emissive layer is:

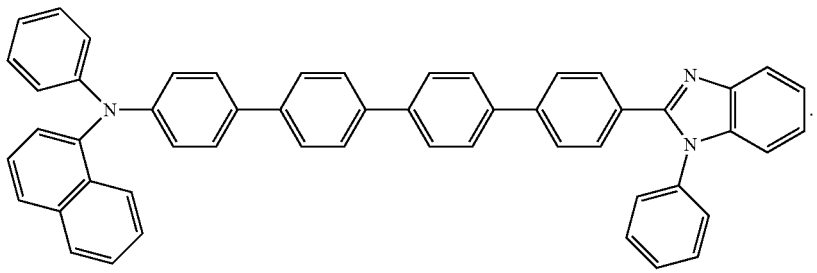

.

20. The emissive construct of claim 1, wherein the phosphorescent red emissive layer comprises a host and at least one dopant.

21. The emissive construct of claim 20, wherein the host of the phosphorescent red emissive layer comprises

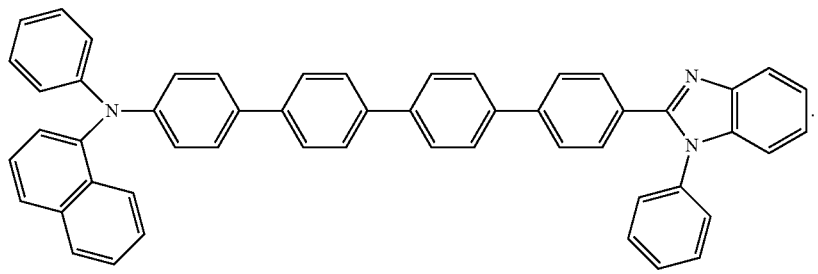 [SMILES: c1ccc(N(c2ccc(-c3ccc(-c4ccc(-c5ccc(-c6nc7ccccc7n6-c6ccccc6)cc5)cc4)cc3)cc2)c2cccc3ccccc23)cc1]

22. The emissive construct of claim 20, wherein the dopant of the phosphorescent red emissive layer comprises Ir(piq)$_2$acac.

23. The emissive construct of claim 20, wherein the phosphorescent red emissive layer comprises about 10% by weight of the dopant.

24. The emissive construct of claim 1, wherein the phosphorescent yellow emissive layer comprises a host and at least one dopant.

25. The emissive construct of claim 24, wherein the host of the phosphorescent yellow emissive layer comprises:

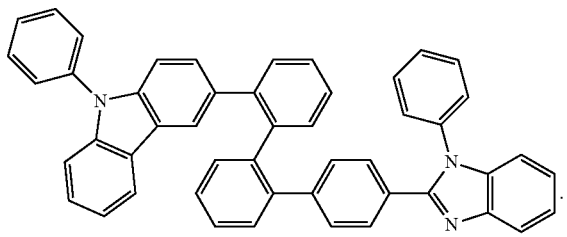

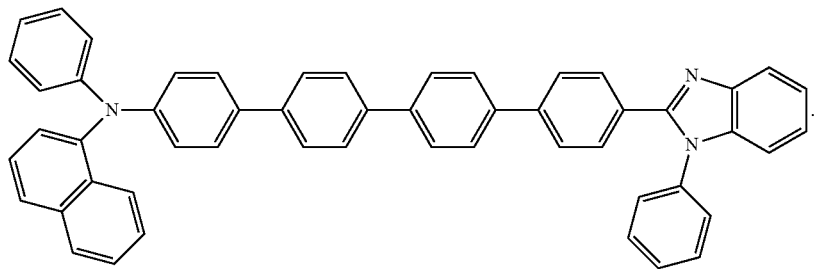 [SMILES: c1ccc(N(c2ccc(-c3ccc(-c4ccc(-c5ccc(-c6nc7ccccc7n6-c6ccccc6)cc5)cc4)cc3)cc2)c2cccc3ccccc23)cc1]

26. The emissive construct of claim 24, wherein the dopant of the phosphorescent yellow emissive layer comprises:

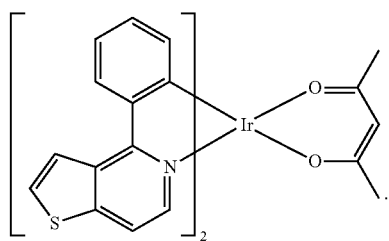

27. The emissive construct of claim 24, wherein the dopant concentration of the phosphorescent yellow emissive layer is about 6%.

28. The emissive construct of claim 1, wherein the phosphorescent green emissive layer comprises a host and at least one dopant.

29. The emissive construct of claim 28, wherein the host of the phosphorescent green emissive layer has T$_1$ level that is higher than about 2.5 eV.

30. The emissive construct of claim 28, wherein the host of the phosphorescent green emissive layer comprises 31. The emissive construct of claim 30, wherein the dopant of the phosphorescent green emissive layer comprises Ir(ppy)$_3$.

32. The emissive construct of claim 30, wherein the dopant of the phosphorescent green emissive layer concentration is about 6%.

33. An emissive construct comprising:
a fluorescent blue emissive layer comprising a host and a dopant, wherein the dopant is

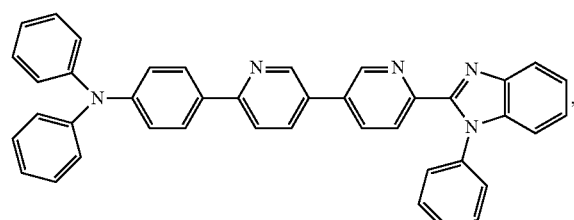

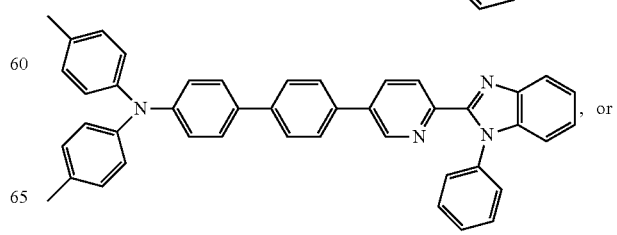

, or

-continued

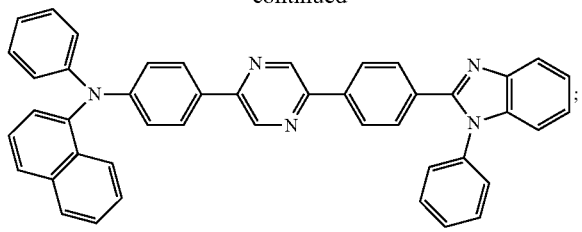

a phosphorescent red emissive layer contacting the fluorescent blue emissive layer;
a phosphorescent green emissive layer contacting the phosphorescent red emissive layer; and
a phosphorescent yellow emissive layer contacting the phosphorescent green emissive layer.

34. The emissive construct of claim 33, wherein the host of the phosphorescent green emissive layer has $T_1$ level that is greater than about 2.3 eV.

35. The emissive construct of claim 33, wherein the host of the phosphorescent green emissive layer has $T_1$ level that is greater than about 2.4 eV.

36. The emissive construct of claim 33, wherein the green emissive layer has a thickness of about 3 nm to about 5 nm.

37. The emissive construct of claim 33, wherein the green emissive layer has a thickness of about 3 nm to about 4 nm.

38. The emissive construct of claim 33, wherein the green emissive layer has a thickness of about 3.5 nm.

39. The emissive construct of claim 33, wherein the fluorescent blue emissive layer has a thickness of at least about 5 nm.

40. The emissive construct of claim 33, wherein the phosphorescent red emissive layer has a thickness of about 0.1 nm to about 10 nm.

41. The emissive construct of claim 33, wherein the phosphorescent yellow emissive layer has a thickness of about 5 nm to about 50 nm.

42. The emissive construct of claim 33, wherein the combined thickness of the fluorescent blue emissive layer and the phosphorescent yellow emissive layer are at least about 70% of the thickness of the emissive construct.

43. The emissive construct of claim 33, wherein the dopant concentration in the fluorescent blue emissive layer is about 0.01 to about 10% by weight.

44. The emissive construct of claim 33, wherein the host is

45. The emissive construct of claim 33, wherein the phosphorescent red emissive layer has a thickness of about 1 nm.

46. The emissive construct of claim 33, wherein the host of the phosphorescent green emissive layer has $T_1$ level that is greater than about 2.25 eV.

47. The emissive construct of claim 33, wherein the dopant comprises:

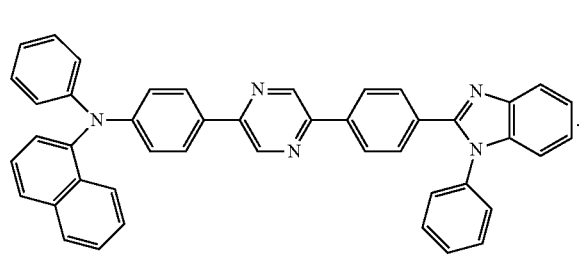 [SMILES: c1ccc(N(c2ccc(-c3cnc(-c4ccc(-c5nc6ccccc6n5-c5ccccc5)cc4)cn3)cc2)c2cccc3ccccc23)cc1]

48. A white light emitting OLED device comprising,
a substrate,
an insulating layer coated on top of the substrate;
a reflective and opaque anode disposed above the insulating layer;
a hole injection layer disposed above the anode;
a hole transport layer disposed above the hole injection layer;
the emissive construct disposed above the hole injection layer, wherein the emissive construct comprises:
a fluorescent blue emissive layer,
a phosphorescent red emissive layer contacting the fluorescent blue emissive layer;
a phosphorescent green emissive layer contacting the phosphorescent red emissive layer; and
a phosphorescent yellow emissive layer contacting the phosphorescent green emissive layer;
an electron transporting layer disposed above the emissive construct;
an electron injection layer disposed above the electron transporting layer;
a semi transparent or transparent cathode disposed above the electron transport layer,

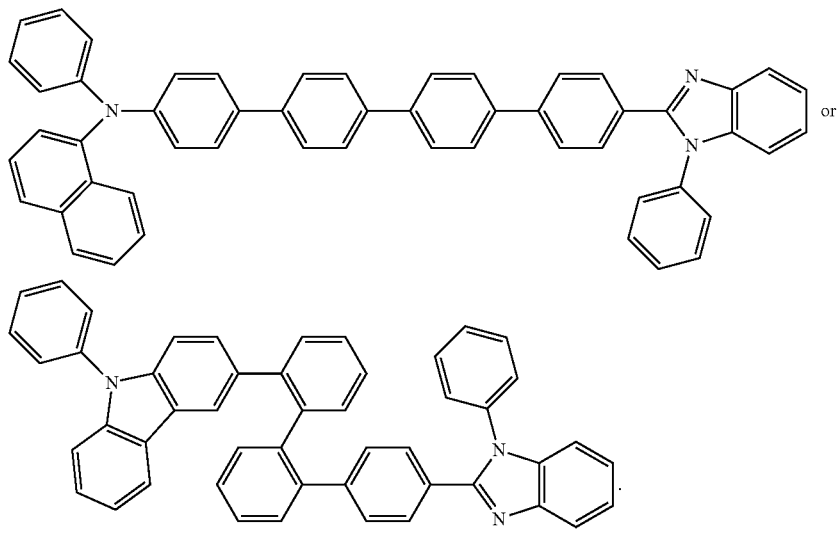

a light emission enhancement layer disposed above the cathode; and
a light scattering layer disposed above the light emission enhancement layer.

49. The white light emitting OLED device of claim 48, wherein the light scattering layer comprises:

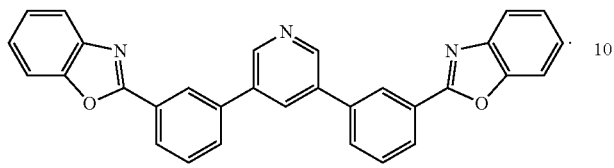

50. The emissive construct of claim 48, wherein the phosphorescent green emissive layer comprises a host having a $T_1$ level that is greater than about 2.35 eV.

51. A white emitting OLED device comprising:
a cathode;
an anode; and
an emissive construct disposed between the anode and cathode;
wherein the emissive construct comprises:
a fluorescent blue emissive layer,
a phosphorescent red emissive layer contacting the fluorescent blue emissive layer;
a phosphorescent green emissive layer contacting the phosphorescent red emissive layer; and
a phosphorescent yellow emissive layer contacting the phosphorescent green emissive layer; and
an outcoupling lens.

52. The emissive construct of claim 51, wherein the phosphorescent green emissive layer comprises a host having a $T_1$ level that is greater than about 2.25 eV.

* * * * *